United States Patent [19]
Bochis et al.

[11] Patent Number: 5,670,504
[45] Date of Patent: Sep. 23, 1997

[54] 2,6-DIARYL PYRIDAZINONES WITH IMMUNOSUPPRESSANT ACTIVITY

[75] Inventors: Richard J. Bochis, East Brunswick; Andrew Kotliar, Somerset; William H. Parsons, Belle Mead; Kathleen Rupprecht, Cranford, all of N.J.

[73] Assignee: Merck & Co. Inc., Rahway, N.J.

[21] Appl. No.: 392,588

[22] Filed: Feb. 23, 1995

[51] Int. Cl.⁶ .................................................. A61K 31/50
[52] U.S. Cl. ........................................... 514/247; 544/240
[58] Field of Search ..................... 544/240, 235; 514/247; A61K 31/50

[56] References Cited

U.S. PATENT DOCUMENTS

| | | | |
|---|---|---|---|
| 4,820,704 | 4/1989 | Richarz et al. | 544/240 |
| 4,910,201 | 3/1990 | Kawamura et al. | 514/247 |
| 4,995,091 | 2/1991 | Makabe | 514/247 |
| 5,169,848 | 12/1992 | Bettarini | 514/247 |
| 5,202,323 | 4/1993 | Tanikawa | 544/240 |
| 5,409,956 | 4/1995 | Yoshida et al. | 514/247 |
| 5,462,914 | 10/1995 | Leitner | 544/240 |
| 5,506,228 | 4/1996 | Norton et al. | 544/240 |

FOREIGN PATENT DOCUMENTS 61-145106  7/1986  Japan ..................... 514/247

OTHER PUBLICATIONS

Elghandour, et al. Chem. Abstr vol. 122 Entry 81263 (1994).
Derwent Abstract of JP67/9344 (1967) AN–66–26853F, Class B.

*Primary Examiner*—Donald G. Daus
*Attorney, Agent, or Firm*—Valerie J. Camara; Mark R. Daniel

[57] ABSTRACT

A class of 2,6-diarylpyridazinones of general structural formula I have been identified that exhibit exhibit immunosuppressant activity with human T-lymphocytes, and are useful as an immunosuppressants.

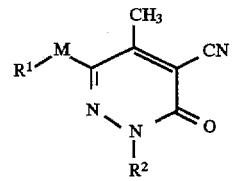

or a pharmaceutically acceptable salt, hydrate or crystal form thereof

6 Claims, No Drawings

2,6-DIARYL PYRIDAZINONES WITH IMMUNOSUPPRESSANT ACTIVITY

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

SUMMARY OF THE INVENTION

A class of 2,6-diarylpyridazinones of general structural formula I have been identified that exhibit exhibit immunosuppressant activity with human T-lymphocytes, and are useful as an immunosuppressants.

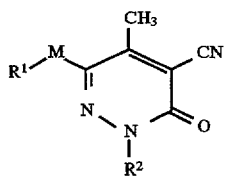

I or a pharmaceutically acceptable salt, hydrate or crystal form thereof, wherein:

$R^1$ and $R^2$ are selected from:

(1) aryl (2) substituted aryl in which as many as three substitutents, X, Y, and Z, may be present, wherein X, Y and Z independently are selected from:

(a) hydrogen, except that when $R^1$ is 4-chlorophenyl, then $R^2$ can not be phenyl;

(b) $C_{1-10}$alkyl, unsubstituted or substituted with one or more substituents selected from:
 (i) aryl,
 (ii) substituted aryl in which the substituents are X', Y' and Z',
 (iii) heteroaryl,
 (iv) substituted heteroaryl in which the substituents are X', Y', and Z',
 (v) unsubstituted or substituted aryloxy, in which the substituents on aryl are X', Y' and Z',
 (vi) unsubstituted or substituted heteroaryloxy, in which the substituents on aryl are X', Y' and Z',
 (vii) $C_{1-6}$ alkoxy,
 (viii) —$OCOC_{1-6}$alkyl,
 (ix) —$OCO_2C_{1-6}$alkyl,
 (x) —$NO_2$
 (xi) —$NR^3R^4$, wherein $R^3$ and $R^4$ are independently selected from:
  (a') hydrogen,
  (b') $C_{1-6}$ alkyl unsubstituted or substituted with one or more of the substituents selected from:
   (i') aryl, which is unsubstituted or substituted with X', Y' and Z'
   (ii') heteroaryl, which is unsubstituted or substituted with X', Y' and Z',
   (iii') —OH
   (iv') —$OR^5$
   (v') —$C_{1-6}$alkoxy
   (vi') —$CO_2H$
   (vii') oxo
   (viii') —$C_{3-7}$cycloalkyl
   (ix') —$C_{1-6}$alkyl—OH
   (x') —$C_{1-6}$alkyl—$OR^5$
  (c') or where $R^3$ and $R^4$ and the N to which they are attached may form an unsubstituted or substituted 3 to 7- membered heterocyclic ring which may include one or two addition heteroatoms independently selected from the group consisting of O, S(O)p, $NR^6$ wherein $R^6$ is hydrogen, or $C_{1-6}$alkyl and p is 0, 1 or 2 such as morpholine, thiomorpholine, piperidine or piperizine
 (xii) —$NR^3COC_{1-6}$alkyl-$R^4$,
 (xiii) —$NR^3CO_2C_{1-6}$alkyl-$R^4$,
 (xiv) —$NR^3CONR^3R^4$,
 (xv) —$OCONR^3R^4$,
 (xvi) —CHO,
 (xvii) —$CO_2H$
 (xviii) —$CONR^3R^4$
 (xix) —OH
 (xx) —$OR^5$,
 (xxi) —$OC_{1-6}$alkylOH,
 (xxii) —$OC_{1-6}$alkyl$OR^5$,
 (xxiii) oxo,
 except that when $R^2$ is 2-methyl-phenyl-, 3-methyl-phenyl, or 4-methyl-phenyl, then $R^1$ can not be 4-chlorophenyl-;

(c) $C_{1-10}$alkyl wherein one or more of the alkyl carbons is replaced by a group selected from —$NR^3$—, —O—, —$S(O)_p$—, —$CO_2$—, —$O_2C$—, —$CONR^3$—, —$NR^3CO$—, —$NR^3CONR^4$—, —CH(OH)—, alkenyl or alkynyl and the alkyl may be unsubstituted or substituted with one or more substituents selected from:

(i) aryl
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) unsubstituted or substituted heteroaryloxy, in which the substituents on aryl are X', Y' and Z',
(vii) $C_{1-6}$ alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO,
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkyl$OR^5$,
(xxiii) oxo (d) $C_{1-10}$alkoxy, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) unsubstituted or substituted heteroaryloxy, in which the substituents on aryl are X', Y' and Z',
(vii) $C_{1-6}$ alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkyl$OR^5$,
(xxiii) oxo, except that when $R^2$ is 4-methoxyphenyl, then $R^1$ is not 4-chlorophenyl, phenyl or —$SO_2$-phenyl;

(e) $C_{1-10}$alkoxy wherein one or more of the alkyl carbons is replaced by a group selected from —$NR^3$—, —O—, —$S(O)_p$—, —$CO_2$—, —$O_2C$—, —$CONR^3$—, —$NR^3CO$—, —$NR^3CONR^4$—, —CH(OH)—, alkenyl or alkynyl and the alkyl may be unsubstituted or substituted with one or more ubstituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) unsubstituted or substituted heteroaryloxy, in which the substiments on aryl are X', Y' and Z',
(vii) $C_{1-6}$alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkyl$OR^5$,
(xxiii) oxo, (f) aryl
(g) substituted aryl wherein the substituents are X', Y' or Z',
(h) aryloxy, (9 substituted aryloxy wherein the substituents are X', Y' or Z',
(j) halogen, except that when $R^2$ is 2-chlorophenyl, 3-chlorophenyl, 4-chlorophenyl or 4-bromophenyl, then $R^1$ is not 4-chlorophenyl;
(k) —$NO_2$, except that when $R^2$ is 3-nitropnehyl, then $R^1$ is not 4-chlorophenyl;
(l) —$NR^3R^4$ wherein $R^3$ and $R^4$ are defined above,
(m) —$NR^3COC_{1-6}$alkyl-$R^4$,
(n) —$NR^3CO_2C_{1-6}$alkyl-$R^4$,
(o) —$NR^3CONR^3R^4$,
(p) —$OCONR^3R^4$,
(q) —CN
(r) —CHO
(s) —$CO_2H$
(t) —$CONR^3R^4$,
(u) —$CF_3$,
(v) —$S(O)_pR^7$, wherein $R^7$ is hydrogen, $C_{1-6}$alkyl, trifluoromethyl, or phenyl and p is 0, 1 or 2.
(x) —$CH(OR^8)(OR^9)$, wherein $R^8$ and $R^9$ are $C_{1-3}$alkyl or taken together form an ethyl or propyl bridge,
(y) $R^3C(O)_n$— wherein $R^3$ is defined above, and n is 1 or 2,
(z) OH
(a") $OR^5$ and
(b") —$R^5$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) $C_{1-6}$alkyl,
(c) $C_{2-6}$alkenyl,
(d) halogen, (e) —NR³R⁴, wherein R³, R⁴, and m are as defined above,
(f) —CN,
(g) —CHO,
(h) —CO₂H
(i) —CONR³R⁴
(j) —CF₃,
(k) —S(O)$_p$R⁷, wherein R⁷ is hydrogen, $C_{1-6}$alkyl, trifluoromethyl, or phenyl, and p is 0, 1 or 2,
(l) —OH
(m) —OR⁵
(n) —R⁵
R⁵ is selected from:
(a) —PO(OH)O³¹M⁺, wherein M⁺ is a positively charged inorganic or organic counterion,
(b) —SO₃⁻M+,
(c) —CO(CH₂)$_q$CO₂⁻M⁺, wherein q is 1–3, and
(d) —CO—$C_{1-6}$alkyl—NR⁶R⁷, wherein R⁶ and R⁷ are as defined above and the alkyl is unsubstituted or substituted with one or more substituents selected from:
  (i) hydroxy,
  (ii) $C_{1-6}$alkoxy,
  (iii) —NR¹⁶R¹⁷, wherein R¹⁶ and R¹⁷ are independently selected from:
    (a') hydrogen, and
    (b') $C_{1-6}$alkyl,
  (iv) —COOR⁶, wherein R⁶ is as defined above,
  (v) phenyl,
  (iv) substituted phenyl in which the substituents are X, Y and Z,
  (vii) heteroaryl,
  (viii) —SH, and
  (ix) —S—$C_{1-6}$alkyl;
M is selected from S(O)$_p$, where p is defined above.
n is 1 or 2.

As an immunosuppressant, these compounds are useful in the treatment of autoimmune diseases, the prevention of rejection of foreign organ transplants and/or related afflictions, diseases and illnesses.

DETAILED DESCRIPTION OF THE INVENTION

A. Scope of the Invention

The present invention is directed to a compound of structural formula I.

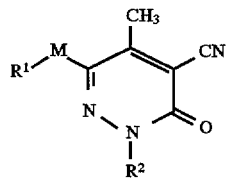

or a pharmaceutically acceptable salt, hydrate or crystal form thereof, wherein:

R¹ and R² are selected from:
(1) aryl
(2) substituted aryl in which as many as three substitutents, X, Y, and Z, may be present, wherein X, Y and Z independently are selected from:
  (a) hydrogen, except that when R¹ is 4-chlorophenyl, then R² can not be phenyl;
  (b) $C_{1-10}$alkyl, unsubstituted or substituted with one or more substituents selected from:

(i) aryl,
  (ii) substituted aryl in which the substituents are X', Y' and Z',
  (iii) heteroaryl,
  (iv) substituted heteroaryl in which the substituents are X', Y', and Z',
  (v) unsubstituted or substituted aryloxy, in which the substituents on aryl are X', Y' and Z',
  (vi) unsubstituted or substituted heteroaryloxy, in which the substituents on aryl are X', Y' and Z',
  (vii) $C_{1-6}$ alkoxy,
  (viii) —OCOC$_{1-6}$alkyl,
  (ix) —OCO₂C$_{1-6}$alkyl,
  (x) —NO₂
  —NR³R⁴, wherein R³ and R⁴ are independently selected from:
    (a') hydrogen,
    (b') $C_{1-6}$ alkyl unsubstituted or substituted with one or more of the substituents selected from:
      (i') aryl, which is unsubstituted or substituted with X', Y' and Z'
      (ii') heteroaryl, which is unsubstituted or substituted with X', Y' and Z',
      (iii') —OH
      (iv') —OR⁵
      (v') —$C_{1-6}$alkoxy
      (vi') —CO₂H
      (vii') oxo
      (viii') —$C_{3-7}$cycloalkyl
      (ix') —$C_{1-6}$alky—OH
      (x') —$C_{1-6}$alkyl—OR⁵
    (c') or where R³ and R⁴ and the N to which they are attached may form an unsubstituted or substituted 3 to 7- membered heterocyclic ring which may include one or two addition heteroatoms independently selected from the group consisting of O, S(O)$_p$, NR⁶ wherein R⁶ is hydrogen, or $C_{1-6}$alkyl and p is 0, 1 or 2 such as morpholine, thiomorpholine, piperidine or piperizine
  (xii) —NR³COC$_{1-6}$alkyl-R⁴,
  (xiii) —NR³ CO₂C$_{1-6}$alkyl-R⁴,
  (xiv) —NR³CONR³R⁴,
  (xv) —OCONR³R⁴,
  (xvi) —CHO,
  (xvii) —CO₂H
  (xviii) —CONR³R⁴
  (xix) —OH
  (xx) —OR⁵,
  (xxi) —OC$_{1-6}$alkylOH,
  (xxii) —OC$_{1-6}$alkylOR⁵,
  (xxiii) oxo,
except that when R² is 2-methyl-phenyl-, 3-methyl-phenyl, or 4-methyl-phenyl, then R¹ can not be 4-chlorophenyl-;
(c) $C_{1-10}$alkyl wherein one or more of the alkyl carbons is replaced by a group selected from —NR³—, —O—, —S(O)$_p$—, —CO₂—, —O₂C—, —CONR³—, —NR³CO—, —NR³CONR⁴—, —CH(OH)—, alkenyl or alkynyl and the alkyl may be unsubstituted or substituted with one or more substituents selected from:
  (i) aryl
  (ii) substituted aryl in which the substituents are X', Y' and Z',
  (iii) heteroaryl,
  (iv) substituted heteroaryl in which the substituents are X', Y', and Z',
  (v) unsubstituted or substituted aryloxy, in which the substituents on aryl are X', Y' and Z', (vi) unsubstituted or substituted heteroaryloxy, in which the substituents on aryl are X', Y' and Z',
(vii) $C_{1-6}$ alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkylOR$^5$,
(xxiii) oxo, (d) $C_{1-10}$alkoxy, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) unsubstituted or substituted heteroaryloxy, in which the substituents on aryl are X', Y' and Z',
(vii) $C_{1-6}$ alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkylOR$^5$,
(xxiii) oxo,
except that when $R^2$ is 4-methoxyphenyl, then $R^1$ is not 4-chlorophenyl, phenyl or -$SO_2$-phenyl;

(e) $C_{1-10}$alkoxy wherein one or more of the alkyl carbons is replaced by a group selected from —$NR^3$—, —O—, —$S(O)_p$—, —$CO_2$—, —$O_2C$—, —$CONR^3$—, —$NR^3CO$—, —$NR^3CONR^4$—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) unsubstituted or substituted heteroaryloxy, in which the substituents on aryl are X', Y' and Z'.

(vii) $C_{1-6}$ alkoxy,
(viii) —$OCOC_{1-6}$alkyl,
(ix) —$OCO_2C_{1-6}$alkyl,
(x) —$NO_2$
(xi) —$NR^3R^4$, wherein $R^3$ and $R^4$ are defined above,
(xii) —$NR^3COC_{1-6}$alkyl-$R_4$,
(xiii) —$NR^3CO_2C_{1-6}$alkyl-$R^4$,
(xiv) —$NR^3CONR^3R^4$,
(xv) —$OCONR^3R^4$,
(xvi) —CHO
(xvii) —$CO_2H$
(xviii) —$CONR^3R^4$
(xix) —OH
(xx) —$OR^5$,
(xxi) —$OC_{1-6}$alkylOH,
(xxii) —$OC_{1-6}$alkylOR$^5$,
(xxiii) oxo, (f) aryl
(g) substituted aryl wherein the substituents are X', Y' or Z',
(g) aryloxy,
(i) substituted aryloxy wherein the substituents are X', Y' or Z',
(j) halogen, except that when $R^2$ is 2-chlorophenyl, 3-chlorophenyl, 4-chlorophenyl or 4-bromophenyl, then $R^1$ is not 4-chlorophenyl;
(k) —$NO_2$, except that when $R^2$ is 3-nitropnehyl, then $R^1$ is not 4-chlorophenyl;
(l) $NR^3R^4$ wherein $R^3$ and $R^4$ are defined above,
(m) —$NR^3COC_{1-6}$alkyl-$R^4$,
(n) —$NR^3CO_2C_{1-6}$alkyl-$R^4$,
(o) —$NR^3CONR^3R^4$,
(p) —$OCONR^3R^4$,
(q) —CN
(r) —CHO
(s) —$CO_2H$
(t) —$CONR^3R^4$,
(u) —$CF_3$,
(v) —$S(O)_pR^7$, wherein $R^7$ is hydrogen, $C_{1-6}$alkyl, trifluoromethyl, or phenyl and p is 0, 1 or 2.
(x) —$CH(OR^8)(OR^9)$, wherein $R^8$ and $R^9$ are $C_{1-3}$alkyl or taken together form an ethyl or propyl bridge,
(y) $R^3C(O)_n$— wherein $R^3$ is defined above, and n is 1 or 2,
(z) OH
(a") $OR^5$ and
(b") —$R^5$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) $C_{1-6}$alkyl,
(c) $C_{2-6}$alkenyl,
(d) halogen,
(e) —$NR^3R^4$, wherein $R^3$, $R^4$, and m are as defined above,
(f) —CN,
(g) —CHO,
(h) —$CO_2H$
(i) —$CONR^3R^4$ (j) —CF₃, (k) —S(O)$_p$R⁷, wherein R⁷ is hydrogen, C$_{1-6}$alkyl, trifluoromethyl, or phenyl, and p is 0, 1 or 2, (l) —OH (m) —OR⁵

(n) —R⁵

R⁵ is selected from:

(a) —PO(OH)O³¹M⁺, wherein M⁺ is a positively charged inorganic or organic counterion, (b) —SO₃⁻M+, (c) —CO(CH₂)$_q$CO₂⁻M⁺, wherein q is 1–3, and (d) —CO—C$_{1-6}$alkyl—NR⁶R⁷, wherein R⁶ and R⁷ are as defined above and the alkyl is unsubstituted or substituted with one or more substituents selected from:
  (i) hydroxy,
  (ii) C$_{1-6}$alkoxy,
  (iii) —NR¹⁶R¹⁷, wherein R¹⁶ and R¹⁷ are independently selected from:
    (a') hydrogen, and
    (b') C$_{1-6}$alkyl,
  (iv) —COOR⁶, wherein R⁶ is as defined above,
  (v) phenyl,
  (iv) substituted phenyl in which the substituents are X, Y and Z,
  (vii) heteroaryl,
  (viii) —SH, and
  (ix) —S—C$_{1-6}$alkyl;

M is selected from S(O)$_p$, where p is defined above.

n is 1 or 2.

The compounds of the present invention may have asymmetric centers and this invention includes all of the optical iomers and mixtures thereof.

In addition compounds with carbon-carbon double bonds may occur in Z- and E- forms with all isomeric forms of the compounds being included in the present invention.

When any variable (e.g., alkyl; aryl, R³, R⁴, R⁵, R⁶, R⁷, R⁸, R⁹, X, Y, Z, X', Y', Z', M, p etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethylpentyl, and the like, and includes E and Z forms, where applicable. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula HNR⁶R⁷).

The aryl group may include phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono- alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, R¹¹O-alkyl, alkoxy, alkoxyalkyl, formamido, alkyl—CO₂—, formamidoalkyl, alkyl—CO₂—alkyl—, carboxyl, alkyl—CO₂H, alkyl—O₂C—, alkyl—O₂C—alkyl—, and OR¹¹.

In the instant combination, preferred compounds of formula I are the compounds identified as follows:

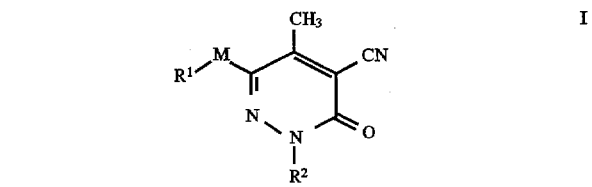

Where M is S, SO or SO₂ and,

| R¹ | R² |
|---|---|
| phenyl | phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-CH₃Ophenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-NO₂phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-CH₃Sphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-CH₃SOphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-CH₃SO₂phenyl |
| 2-methylphenyl | " |
| 3-methylphenyl | " |
| 4-methylphenyl | " |
| 3,4-dimethylphenyl | " |
| 3,5-dimethylphenyl | " |
| 2-methylphenyl | 4-CH₃Ophenyl |
| 3-methylphenyl | " |
| 4-methylphenyl | " |
| 3,4-dimethylphenyl | " |
| 3,5-dimethylphenyl | " |
| phenyl | 4-NO₂phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 4-CH₃Sphenyl |
| 2-methylphenyl | " |
| 3-methylphenyl | " |

| R¹ | R² |
|---|---|
| 4-methylphenyl | " |
| 3,4-dimethylphenyl | " |
| 3,5-dimethylphenyl | " |
| phenyl | 4-CH₃SOphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 4-CH₃SO₂phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3,4-OCH₂Ophenyl |
| 2-methylphenyl | " |
| 3-methylphenyl | " |
| 4-methylphenyl | " |
| 3,4-dimethylphenyl | " |
| 3,5-dimethylphenyl | " |
| 2-CH₃Ophenyl | Phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-CH₃Ophenyl |
| 3-CH₃Ophenyl | " |
| 4-CH₃Ophenyl | " |
| 3,4-bis-CH₃Ophenyl | " |
| 3,5-bisCH₃Ophenyl | " |
| 2-CH₃Ophenyl | 3-NO₂phenyl |
| 3-CH₃Ophenyl | " |
| 4-CH₃Ophenyl | " |
| 3,4-bis-CH₃Ophenyl | " |
| 3,5-bisCH₃Ophenyl | " |
| 2-CH₃Ophenyl | 3-CH₃Sphenyl |
| 3-CH₃Ophenyl | " |
| 4-CH₃Ophenyl | " |
| 3,4-bis-CH₃Ophenyl | " |
| 3,5-bisCH₃Ophenyl | " |
| 2-CH₃Ophenyl | 3-CH₃SOphenyl |
| 3-CH₃Ophenyl | " |
| 4-CH₃Ophenyl | " |
| 3,4-bis-CH₃Ophenyl | " |
| 3,5-bisCH₃Ophenyl | " |
| 2-CH₃Ophenyl | 3-CH₃SO₂phenyl |
| 3-CH₃Ophenyl | " |
| 4-CH₃Ophenyl | " |
| 3,4-bis-CH₃Ophenyl | " |
| 3,5-bisCH₃Ophenyl | " |
| 2-CH₃Ophenyl | 4-CH₃Ophenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Ophenyl | 4-NO₂phenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Ophenyl | 4-CH₃Sphenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Ophenyl | 4-CH₃SOphenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Ophenyl | 4-CH₃SO₂phenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Ophenyl | 3,4-CH₂OCH₂phenyl |
| 3-CH₃Ophenyl | " |
| 4-CH₃Ophenyl | " |
| 3,4-bisCH₃Ophenyl | " |
| 3,5-bisCH₃Ophenyl | " |
| 2-CH₃Sphenyl | Phenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 3-CH₃Ophenyl |
| 3-CH₃Sphenyl | " |
| 4-CH₃Sphenyl | " |
| 3,4-bis-CH₃Sphenyl | " |
| 3,5-bisCH₃Sphenyl | " |
| 2-CH₃Sphenyl | 3-NO₂phenyl |
| 3-CH₃Sphenyl | " |
| 4-CH₃Sphenyl | " |
| 3,4-bis-CH₃Sphenyl | " |
| 3,5-bisCH₃Sphenyl | " |
| 2-CH₃Sphenyl | 3-CH₃Sphenyl |
| 3-CH₃Sphenyl | " |
| 4-CH₃Sphenyl | " |
| 3,4-bis-CH₃Sphenyl | " |
| 3,5-bisCH₃Sphenyl | " |
| 2-CH₃Sphenyl | 3-CH₃SOphenyl |
| 3-CH₃Sphenyl | " |
| 4-CH₃Sphenyl | " |
| 3,4-bis-CH₃Sphenyl | " |
| 3,5-bisCH₃Sphenyl | " |
| 2-CH₃Sphenyl | 3-CH₃SO₂phenyl |
| 3-CH₃Sphenyl | " |
| 4-CH₃Sphenyl | " |
| 3,4-bis-CH₃Sphenyl | " |
| 3,5-bisCH₂Sphenyl | " |
| 2-CH₃Sphenyl | 4-CH₃Ophenyl |
| 3-CH₃Sphenyl | " |
| 4-CH₃Sphenyl | " |
| 3,4-bisCH₃Sphenyl | " |
| 3,5-bisCH₃Sphenyl | " |
| 2-CH₃Sphenyl | 4-NO₂phenyl |
| 3-CH₃Sphenyl | " |
| 4-CH₃Sphenyl | " |
| 3,4-bisCH₃Sphenyl | " |
| 3,5-bisCH₃Sphenyl | " |
| 2-CH₃Sphenyl | 4-CH₃Sphenyl |
| 3-CH₃Sphenyl | " |
| 4-CH₃Sphenyl | " |
| 3,4-bisCH₃SPhenyl | " |
| 3,5-bisCH₃Sphenyl | " |
| 2-CH₃Sphenyl | 4-CH₃SOphenyl |
| 3-CH₃Sphenyl | " |
| 4-CH₃Sphenyl | " |
| 3,4-bisCH₃Sphenyl | " |
| 3,5-bisCH₃Sphenyl | " |
| 2-CH₃Sphenyl | 4-CH₃SO₂phenyl |
| 3-CH₃Sphenyl | " |
| 4-CH₃Sphenyl | " |
| 3,4-bisCH₃Sphenyl | " |
| 3,5-bisCH₃Sphenyl | " |
| 2-CH₃Sphenyl | 3,4-CH₂OCH₂phenyl |
| 3-CH₃Sphenyl | " |
| 4-CH₃Sphenyl | " |
| 3,4-bisCH₃Sphenyl | " |
| 3,5-bisCH₃Sphenyl | " |
| 2-CH₃SOphenyl | Phenyl |
| 3-CH₃SOphenyl | " |
| 4-CH₃SOphenyl | " |
| 3,4-bis-CH₃Sphenyl | " |
| 3,5-bis-CH₃Sphenyl | " |
| 2-CH₃SOphenyl | 3-CH₃Ophenyl |
| 3-CH₃SOphenyl | " |
| 4-CH₃SOphenyl | " |
| 3,4-bis-CH₃SOphenyl | " |
| 3,5-bisCH₃SOphenyl | " |
| 2-CH₃SOphenyl | 3-NO₂phenyl |
| 3-CH₃SOphenyl | " |
| 4-CH₃SOphenyl | " |
| 3,4-bis-CH₃SOphenyl | " |
| 3,5-bisCH₃SOphenyl | " |

-continued

| R¹ | R² |
|---|---|
| 2-CH₃SOphenyl | 3-CH₃Sphenyl |
| 3-CH₃SOphenyl | " |
| 4-CH₃SOphenyl | " |
| 3,4-bis-CH₃SOphenyl | " |
| 3,5-bisCH₃SOphenyl | " |
| 2-CH₃SOphenyl | 3-CH₃SOphenyl |
| 3-CH₃SOphenyl | " |
| 4-CH₃SOphenyl | " |
| 3,4-bis-CH₃SOphenyl | " |
| 3,5-bisCH₃SOphenyl | " |
| 2-CH₃SOphenyl | 3-CH₃SO₂phenyl |
| 3-CH₃SOphenyl | " |
| 4-CH₃SOphenyl | " |
| 3,4-bis-CH₃SOphenyl | " |
| 3,5-bisCH₃SOphenyl | " |
| 2-CH₃SOphenyl | 4-CH₃Ophenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SOphenyl | 4-NO₂phenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SOphenyl | 4-CH₃Sphenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SOphenyl | 4-CH₃SOphenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SOphenyl | 4-CH₃SO₂phenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SOphenyl | 3,4-CH₂OCH₂phenyl |
| 3-CH₃SOphenyl | " |
| 4-CH₃SOphenyl | " |
| 3,4-bisCH₃SOphenyl | " |
| 3,5-bisCH₃SOphenyl | " |
| 2-CH₃SO₂phenyl | Phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 3-CH₃Ophenyl |
| 3-CH₃SO₂phenyl | " |
| 4-CH₃SO₂phenyl | " |
| 3,4-bis-CH₃SO₂phenyl | " |
| 3,5-bisCH₃SO₂phenyl | " |
| 2-CH₃SO₂phenyl | 3-NO₂phenyl |
| 3-CH₃SO₂phenyl | " |
| 4-CH₃SO₂phenyl | " |
| 3,4-bis-CH₃SO₂phenyl | " |
| 3,5-bisCH₃SO₂phenyl | " |
| 2-CH₃SO₂phenyl | 3-CH₃Sphenyl |
| 3-CH₃SO₂phenyl | " |
| 4-CH₃SO₂phenyl | " |
| 3,4-bis-CH₃SO₂phenyl | " |
| 3,5-bisCH₃SO₂phenyl | " |
| 2-CH₃SO₂phenyl | 3-CH₃SOphenyl |
| 3-CH₃SO₂phenyl | " |
| 4-CH₃SO₂phenyl | " |
| 3,4-bis-CH₃SO₂phenyl | " |
| 3,5-bisCH₃SO₂phenyl | " |
| 2-CH₃SO₂phenyl | 3-CH₃SO₂phenyl |
| 3-CH₃SO₂phenyl | " |
| 4-CH₃SO₂phenyl | " |
| 3,4-bis-CH₃SO₂phenyl | " |
| 3,5-bisCH₃SO₂phenyl | " |
| 2-CH₃SO₂phenyl | 4-CH₃Ophenyl |
| 3-CH₃SO₂Phenyl | " |
| 4-CH₃SO₂phenyl | " |

-continued

| R¹ | R² |
|---|---|
| 3,4-bisCH₃SO₂phenyl | " |
| 3,5-bisCH₃SO₂phenyl | " |
| 2-CH₃SO₂phenyl | 4-NO₂phenyl |
| 3-CH₃SO₂phenyl | " |
| 4-CH₃SO₂phenyl | " |
| 3,4-bisCH₃SO₂phenyl | " |
| 3,5-bisCH₃SO₂phenyl | " |
| 2-CH₃SO₂phenyl | 4-CH₃Sphenyl |
| 3-CH₃SO₂phenyl | " |
| 4-CH₃SO₂phenyl | " |
| 3,4-bisCH₃SO₂phenyl | " |
| 3,5-bisCH₃SO₂phenyl | " |
| 2-CH₃SO₂phenyl | 4-CH₃SOphenyl |
| 3-CH₃SO₂phenyl | " |
| 4-CH₃SO₂phenyl | " |
| 3,4-bisCH₃SO₂phenyl | " |
| 3,5-bisCH₃SO₂phenyl | " |
| 2-CH₃SO₂phenyl | 4-CH₃SO₂phenyl |
| 3-CH₃SO₂phenyl | " |
| 4-CH₃SO₂phenyl | " |
| 3,4-bisCH₃SO₂phenyl | " |
| 3,5-bisCH₃SO₂phenyl | " |
| 2-CH₃SO₂phenyl | 3,4-CH₂OCH₂phenyl |
| 3-CH₃SO₂phenyl | " |
| 4-CH₃SO₂phenyl | " |
| 3,4-bisCH₃SO₂phenyl | " |
| 3,5-bisCH₃SO₂phenyl | " |
| 2-Clphenyl | phenyl |
| 3-Clphenyl | " |
| 3,4-di-Clphenyl | " |
| 3,5-diClphenyl | " |
| 2-Clphenyl | 3-CH₃Ophenyl |
| 3-Clphenyl | " |
| 4-Clphenyl | " |
| 3,4-di-Clphenyl | " |
| 3,5-Clphenyl | " |
| 2-Clphenyl | 3-NO₂phenyl |
| 3-Clphenyl | " |
| 3,4-di-Clphenyl | " |
| 3,5-Clphenyl | " |
| 2-Clphenyl | 3-CH₃Sphenyl |
| 3-Clphenyl | " |
| 4-Clphenyl | " |
| 3,4-di-Clphenyl | " |
| 3,5-Clphenyl | " |
| 2-Clphenyl | 3-CH₃SOphenyl |
| 3-Clphenyl | " |
| 4-Clphenyl | " |
| 3,4-di-Ciphenyl | " |
| 3,5-Clphenyl | " |
| 2-Clphenyl | 3-CH₃SO₂phenyl |
| 3-Clphenyl | " |
| 4-Clphenyl | " |
| 3,4-di-Clphenyl | " |
| 3,5-Clphenyl | " |
| 2-Clphenyl | 4-CH₃Ophenyl |
| 3-Clphenyl | " |
| 3,4-Clphenyl | " |
| 3,5-Clphenyl | " |
| 2-Clphenyl | 4-NO₂Phenyl |
| 3-Clphenyl | " |
| 4-Clphenyl | " |
| 3,4-Clphenyl | " |
| 3,5-Clphenyl | " |
| 2-Clphenyl | 4-CH₃Sphenyl |
| 3-Clphenyl | " |
| 4-Clphenyl | " |
| 3,4-Clphenyl | " |
| 3,5-Clphenyl | " |
| 2-Clphenyl | 4-CH₃SOphenyl |
| 3-Clphenyl | " |
| 4-Clphenyl | " |
| 3,4-Clphenyl | " |
| 3,5-Clphenyl | " |
| 2-Clphenyl | 4-CH₃SO₂phenyl |
| 3-Clphenyl | " |
| 4-Clphenyl | " |
| 3,4-Clphenyl | " |

-continued

| R¹ | R² |
|---|---|
| 3,5-Clphenyl | " |
| 2-Clphenyl | 3,4-CH₂OCH₂phenyl |
| 3-Clphenyl | " |
| 4-Clphenyl | " |
| 3,4-Clphenyl | " |
| 3,5-Clphenyl | " |
| 2-CF₃phenyl | phenyl |
| 3-CF₃phenyl | " |
| 4-CF₃phenyl | " |
| 3,4-di-CF₃phenyl | " |
| 3,5-diCF₃phenyl | " |
| 2-CF₃phenyl | 3-CH₃Ophenyl |
| 3-CF₃phenyl | " |
| 4-CF₃phenyl | " |
| 3,4-di-CF₃phenyl | " |
| 3,5-CF₃phenyl | " |
| 2-CF₃phenyl | 3-NO₂phenyl |
| 3-CF₃phenyl | " |
| 4-CF₃phenyl | " |
| 3,4-di-CF₃phenyl | " |
| 3,5-CF₃phenyl | " |
| 2-CF₃phenyl | 3-CH₃Sphenyl |
| 3-CF₃Phenyl | " |
| 4-CF₃phenyl | " |
| 3,4-di-CF₃phenyl | " |
| 3,5-CF₃phenyl | " |
| 2-CF₃phenyl | 3-CH₃SOphenyl |
| 3-CF₃Phenyl | " |
| 4-CF₃phenyl | " |
| 3,4-di-CF₃phenyl | " |
| 3,5-CF₃phenyl | " |
| 2-CF₃phenyl | 3-CH₃SO₂phenyl |
| 3-CF₃phenyl | " |
| 4-CF₃phenyl | " |
| 3,4-di-CF₃phenyl | " |
| 3,5-CF₃phenyl | " |
| 2-CF₃phenyl | 4-CH₃Ophenyl |
| 3-CF₃phenyl | " |
| 4-CF₃phenyl | " |
| 3,4-CF₃phenyl | " |
| 3,5-CF₃phenyl | " |
| 2-CF₃phenyl | 4-NO₂phenyl |
| 3-CF₃Phenyl | " |
| 4-CF₃phenyl | " |
| 3,4-CF₃phenyl | " |
| 3,5-CF₃phenyl | " |
| 2-CF₃phenyl | 4-CH₃Sphenyl |
| 3-CF₃phenyl | " |
| 4-CF₃phenyl | " |
| 3,4-CF₃phenyl | " |
| 3,5-CF₃phenyl | " |
| 2-CF₃phenyl | 4-CH₃SOphenyl |
| 3-CF₃phenyl | " |
| 4-CF₃phenyl | " |
| 3,4-CF₃phenyl | " |
| 3,5-CF₃phenyl | " |
| 2-CF₃phenyl | 4-CH₃SO₂phenyl |
| 3-CF₃phenyl | " |
| 4-CF₃phenyl | " |
| 3,4-CF₃phenyl | " |
| 3,5-CF₃phenyl | " |
| 2-CF₃phenyl | 3,4-CH₂OCH₂phenyl |
| 3-CF₃phenyl | " |
| 4-CF₃phenyl | " |
| 3,4-CF₃phenyl | " |
| 3,5-CF₃phenyl | " |
| 2-Fphenyl | phenyl |
| 3-Fphenyl | " |
| 4-Fphenyl | " |
| 3,4-di-Fphenyl | " |
| 3,5-diFphenyl | " |
| 2-Fphenyl | 3-CH₃Ophenyl |
| 3-Fphenyl | " |
| 4-Fphenyl | " |
| 3,4-di-Fphenyl | " |
| 3,5-Fphenyl | " |
| 2-Fphenyl | 3-NO₂phenyl |
| 3-Fphenyl | " |
| 4-Fphenyl | " |
| 3,4-di-Fphenyl | " |
| 3,5-Fphenyl | " |
| 2-Fphenyl | 3-CH₃Sphenyl |
| 3-Fphenyl | " |
| 4-Fphenyl | " |
| 3,4-di-Fphenyl | " |
| 3,5-Fphenyl | " |
| 2-Fphenyl | 3-CH₃SOphenyl |
| 3-Fphenyl | " |
| 4-Fphenyl | " |
| 3,4-di-Fphenyl | " |
| 3,5-Fphenyl | " |
| 2-Fphenyl | 3-CH₃SO₂phenyl |
| 3-Fphenyl | " |
| 4-Fphenyl | " |
| 3,4-di-Fphenyl | " |
| 3,5-Fphenyl | " |
| 2-Fphenyl | 4-CH₃Ophenyl |
| 3-Fphenyl | " |
| 4-Fphenyl | " |
| 3,4-Fphenyl | " |
| 3,5-Fphenyl | " |
| 2-Fphenyl | 4-NO₂phenyl |
| 3-Fphenyl | " |
| 4-Fphenyl | " |
| 3,4-Fphenyl | " |
| 3,5-Fphenyl | " |
| 2-Fphenyl | 4-CH₃SOphenyl |
| 3-Fphenyl | " |
| 4-Fphenyl | " |
| 3,4-Fphenyl | " |
| 3,5-Fphenyl | " |
| 2-Fphenyl | 4-CH₃SO₂phenyl |
| 3-Fphenyl | " |
| 4-Fphenyl | " |
| 3,4-Fphenyl | " |
| 3,5-Fphenyl | " |
| 2-Fphenyl | 3,4-CH₂OCH₂phenyl |
| 3-Fphenyl | " |
| 4-Fphenyl | " |
| 3,4-Fphenyl | " |
| 3,5-Fphenyl | " |
| 2-ethylphenyl | phenyl |
| 3-ethylphenyl | " |
| 4-ethylphenyl | " |
| 3,4-diethylphenyl | " |
| 3,5-diethylphenyl | " |
| 2-ethylphenyl | 3-CH₃Ophenyl |
| 3-ethylphenyl | " |
| 4-ethylphenyl | " |
| 3,4-diethylphenyl | " |
| 3,5-diethylphenyl | " |
| 2-ethylphenyl | 3-NO₂phenyl |
| 3-ethylphenyl | " |
| 4-ethylphenyl | " |
| 3,4-diethylphenyl | " |
| 3,5-diethylphenyl | " |
| 2-ethylphenyl | 3-CH₃Sphenyl |
| 3-ethylphenyl | " |
| 4-ethylphenyl | " |
| 3,4-diethylphenyl | " |
| 3,5-diethylphenyl | " |
| 2-ethylphenyl | 3-CH₃SOphenyl |
| 3-ethylphenyl | " |
| 4-ethylphenyl | " |
| 3,4-diethylphenyl | " |
| 3,5-diethylphenyl | " |
| 2-ethylphenyl | 3-CH₃SO₂phenyl |
| 3-ethylphenyl | " |
| 4-ethylphenyl | " |
| 3,4-diethylphenyl | " |
| 3,5-diethylphenyl | " |
| 2-ethylphenyl | 4-CH₃Ophenyl |
| 3-ethylphenyl | " |
| 4-ethylphenyl | " |
| 3,4-diethylphenyl | " |
| 3,5-diethylphenyl | " |

-continued

| R¹ | R² |
|---|---|
| 2-ethylphenyl | 4-NO₂phenyl |
| 3-ethylphenyl | " |
| 4-ethylphenyl | " |
| 3,4-diethylphenyl | " |
| 3,5-diethylphenyl | " |
| 2-ethylphenyl | 4-CH₃Sphenyl |
| 3-ethylphenyl | " |
| 4-ethylphenyl | " |
| 3,4-diethylphenyl | " |
| 3,5-diethylphenyl | " |
| 2-ethylphenyl | 4-CH₃SOphenyl |
| 3-ethylphenyl | " |
| 4-ethylphenyl | " |
| 3,4-diethylphenyl | " |
| 3,5-diethylphenyl | " |
| 2-ethylphenyl | 4-CH₃SO₂phenyl |
| 3-ethylphenyl | " |
| 4-ethylphenyl | " |
| 3,4-diethylphenyl | " |
| 3,5-diethylphenyl | " |
| 2-ethylphenyl | 3,4-CHOCH₂phenyl |
| 3-ethylphenyl | " |
| 4-ethylphenyl | " |
| 3,4-diethylphenyl | " |
| 3,5-diethylphenyl | " |
| 2-phenylphenyl | phenyl |
| 3-phenylphenyl | " |
| 4-phenylphenyl | " |
| 2-phenylphenyl | 3-CH₃Ophenyl |
| 3-phenylphenyl | " |
| 4-phenylphenyl | " |
| 2-phenylphenyl | 3-NO₂phenyl |
| 3-phenylphenyl | " |
| 4-phenylphenyl | " |
| 2-phenylphenyl | 3-CH₃Sphenyl |
| 3-phenylphenyl | " |
| 4-phenylphenyl | " |
| 2-phenylphenyl | 3-CH₃SOphenyl |
| 3-phenylphenyl | " |
| 4-phenylphenyl | " |
| 2-phenylphenyl | 3-CH₃SO₂phenyl |
| 3-phenylphenyl | " |
| 4-phenylphenyl | " |
| 2-phenylphenyl | 4-CH₃Ophenyl |
| 3-phenylphenyl | " |
| 4-phenylphenyl | " |
| 2-phenylphenyl | 4-NO₂phenyl |
| 3-phenylphenyl | " |
| 4-phenylphenyl | " |
| 2-phenylphenyl | 4-CH₃Sphenyl |
| 3-phenylphenyl | " |
| 4-phenylphenyl | " |
| 2-phenylphenyl | 4-CH₃SOphenyl |
| 3-phenylphenyl | " |
| 4-phenylphenyl | " |
| 2-phenylphenyl | 4-CH₃SO₂phenyl |
| 3-phenylphenyl | " |
| 4-phenylphenyl | " |
| 2-phenylphenyl | 3,4-CH₂OCH₂Phenyl |
| 3-phenylphenyl | " |
| 4-phenylphenyl | " |
| 2-phenoxyphenyl | phenyl |
| 3-phenoxyphenyl | " |
| 4-phenoxyphenyl | " |
| 2-phenoxyphenyl | 3-CH₃Ophenyl |
| 3-phenoxyphenyl | " |
| 4-phenoxyphenyl | " |
| 2-phenoxyphenyl | 3-NO₂phenyl |
| 3-phenoxyphenyl | " |
| 4-phenoxyphenyl | " |
| 2-phenoxyphenyl | 3-CH₃Sphenyl |
| 3-phenoxyphenyl | " |
| 4-phenoxyphenyl | " |
| 2-phenoxyphenyl | 3-CH₃SOphenyl |
| 3-phenoxyphenyl | " |
| 4-phenoxyphenyl | " |
| 2-phenoxyphenyl | 3-CH₃SO₂phenyl |
| 3-phenoxyphenyl | " |

-continued

| R¹ | R² |
|---|---|
| 4-phenoxyphenyl | " |
| 2-phenoxyphenyl | 4-CH₃Ophenyl |
| 3-phenoxyphenyl | " |
| 4-phenoxyphenyl | " |
| 2-phenoxyphenyl | 4-NO₂phenyl |
| 3-phenoxyphenyl | " |
| 4-phenoxyphenyl | " |
| 2-phenoxyphenyl | 4-CH₃Sphenyl |
| 3-phenoxyphenyl | " |
| 4-phenoxyphenyl | " |
| 2-phenoxyphenyl | 4-CH₃SOphenyl |
| 3-phenoxyphenyl | " |
| 4-phenoxyphenyl | " |
| 2-phenoxyphenyl | 4-CH₃SO₂phenyl |
| 3-phenoxyphenyl | " |
| 4-phenoxyphenyl | " |
| 2-phenoxyphenyl | 3,4-CH₂OCH₂phenyl |
| 3-phenoxyphenyl | " |
| 4-phenoxyphenyl | " |
| naphth-1-yl | phenyl |
| " | 3-CH₃Ophenyl |
| " | 3-NO₂phenyl |
| " | 3-CH₃Sphenyl |
| " | 3-CH₃SO₂phenyl |
| " | 4-CH₃Ophenyl |
| " | 4-NO₂phenyl |
| " | 4-CH₃Sphenyl |
| " | 4-CH₃SO₂phenyl |
| " | 3,4-CH₂OCH₂Phenyl |
| naphth-2-yl | phenyl |
| " | 3-CH₃Ophenyl |
| " | 3-NO₂phenyl |
| " | 3-CH₃Sphenyl |
| " | 3-CH₃SO₂phenyl |
| " | 4-CH₃Ophenyl |
| " | 4-NO₂phenyl |
| " | 4-CH₃Sphenyl |
| " | 4-CH₃SO₂phenyl |
| " | 3,4-CH₂OCH₂phenyl |
| 5-methylnaphth-1-yl | phenyl |
| " | 3-CH₃Ophenyl |
| " | 3-NO₂Phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-methylnaphth-1-yl | phenyl |
| " | 3-CH₃Ophenyl |
| " | 3-NO₂phenyl |

| R¹ | R² |
|---|---|
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂Phenyl |
| " | 3,4-OCH₂Ophenyl |
| 8-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃SPhenyl |
| " | 4-CH₃SOphenyl |
| " | 4-CH₃SO₂phenyl |
| " | 3,4-OCH₂Ophenyl |
| 8-CH₃Onaphth-1-yl | phenyl |
| " | 3-CH₃Ophenyl |
| " | 3-NO₂phenyl |
| " | 3-CH₃SPhenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-methylnaphth-2-yl | phenyl |
| " | 3-CH₃Ophenyl |
| " | 3-NO₂phenyl |

-continued

| R¹ | R² |
|---|---|
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-chloronaphth-2-yl | phenyl |
| " | 3-CH₃Ophenyl |
| " | 3-NO₂Phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |

-continued

| R¹ | R² |
|---|---|
| " | 4-CH₃SOphenyl |
| " | 4-CH₃SO₂phenyl |
| " | 3,4-OCH₂Ophenyl |
| 7-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂Phenyl |
| " | 3,4-OCH₂Ophenyl |
| 5-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-CH₃Onaphth-2-yl | phenyl |
| " | 3-CH₃Ophenyl |
| " | 3-NO₂phenyl |

| R¹ | R² |
|---|---|
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |

Compounds of this invention can be synthesized using the general reaction schemes displayed below.

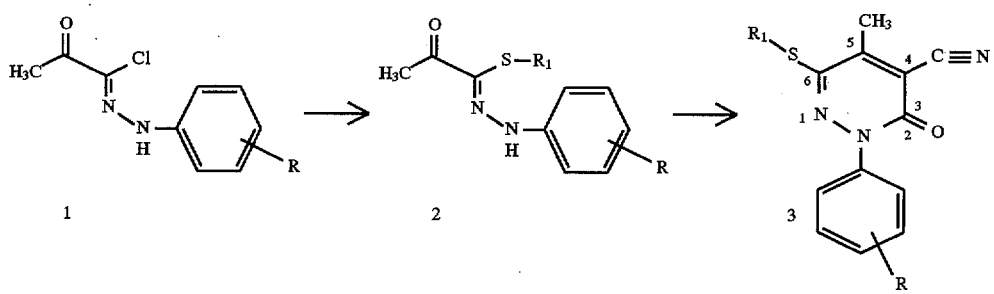

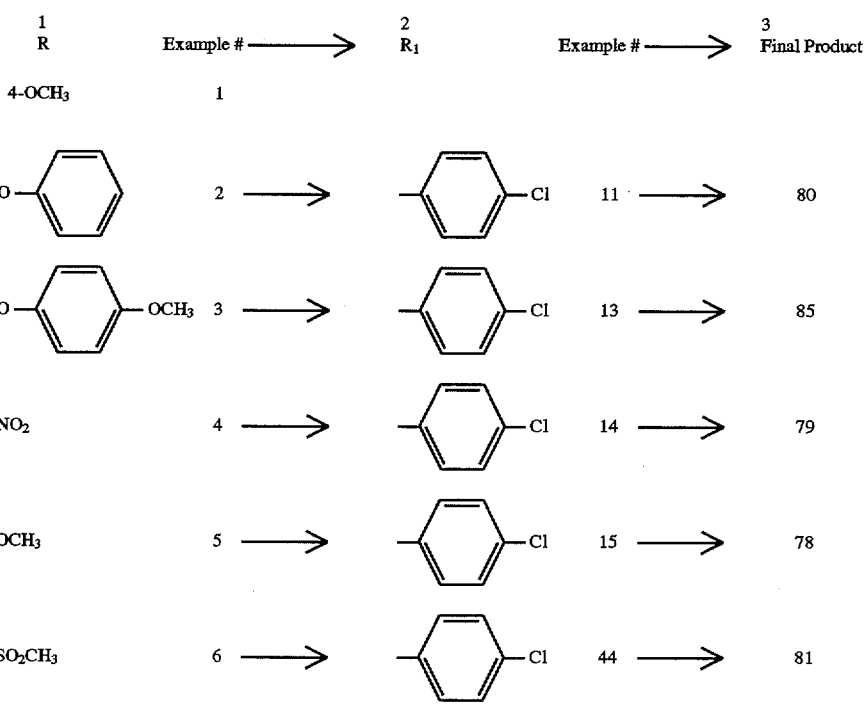

| 1 R | Example # | R₁ | Example # | Final Product |
|---|---|---|---|---|
| 4-OCH₃ | 1 | | | |
| 4-O-phenyl | 2 | phenyl-Cl | 11 | 80 |
| 4-O-phenyl-OCH₃ | 3 | phenyl-Cl | 13 | 85 |
| 4-NO₂ | 4 | phenyl-Cl | 14 | 79 |
| 3-OCH₃ | 5 | phenyl-Cl | 15 | 78 |
| 4-SO₂CH₃ | 6 | phenyl-Cl | 44 | 81 |

-continued
| | | | | | |
|---|---|---|---|---|---|
| 3,4-O—CH₂O— | 7 | → | 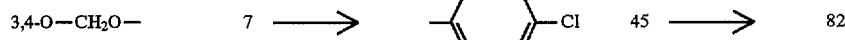 4-Cl | 45 | → 82 |
| 4-SCH₃ | 8 | → | 4-Cl | 12 | → 83 |
| 4-O—C(CH₃)₃ | 9 | → | 4-Cl | 16 | → 84 |
| 4-O—C₂H₅ | | → | 4-Cl | | → 50 |
| 4-OH | | | 4-Cl | | → 49 |
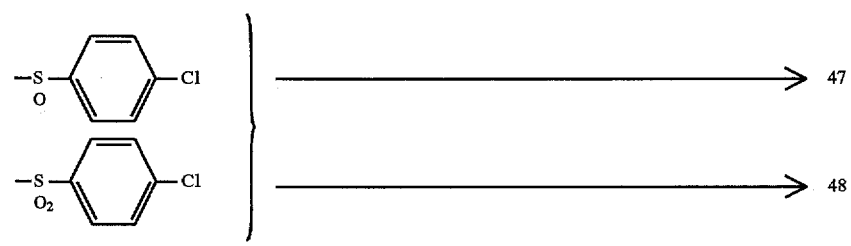
→ 47
→ 48
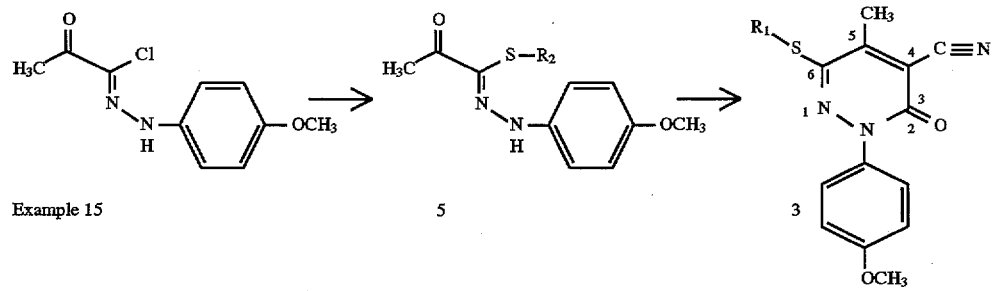
| | Example 15 | | 5 | | 3 |
| 5 R₁ | Example # → | 3 Final Example # |
|---|---|---|
| 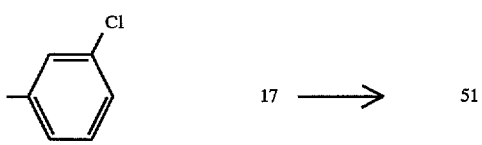 3-Cl | 17 → | 51 |
| 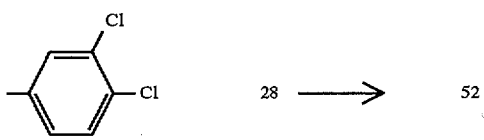 3,4-diCl | 28 → | 52 |
| 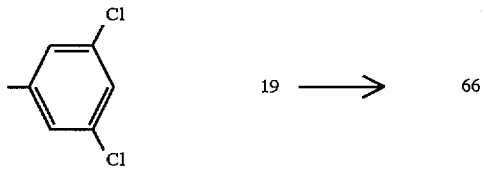 3,5-diCl | 19 → | 66 |

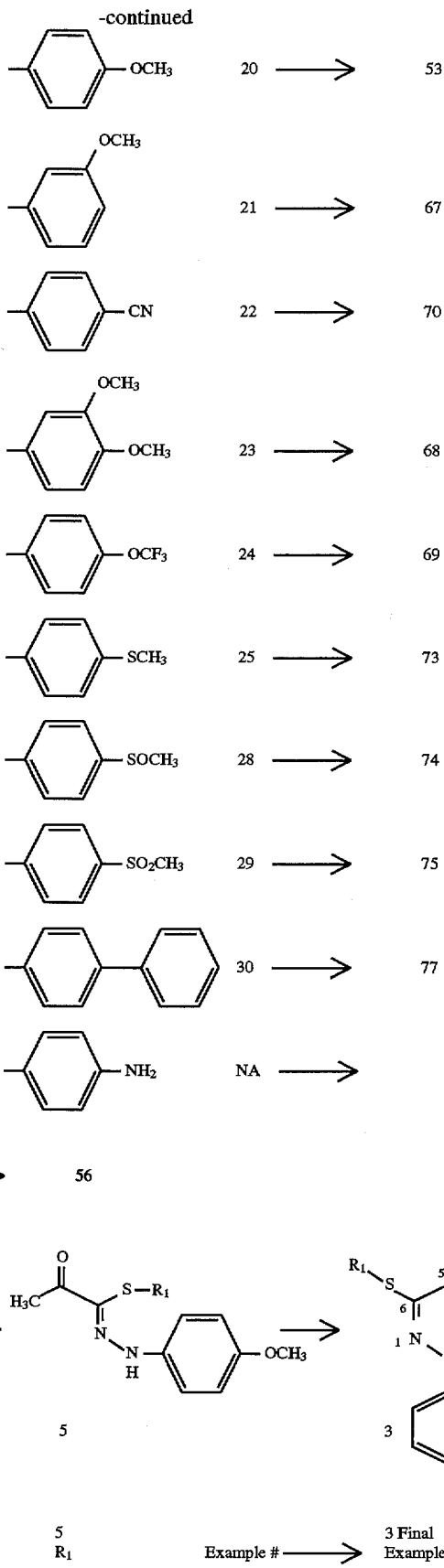

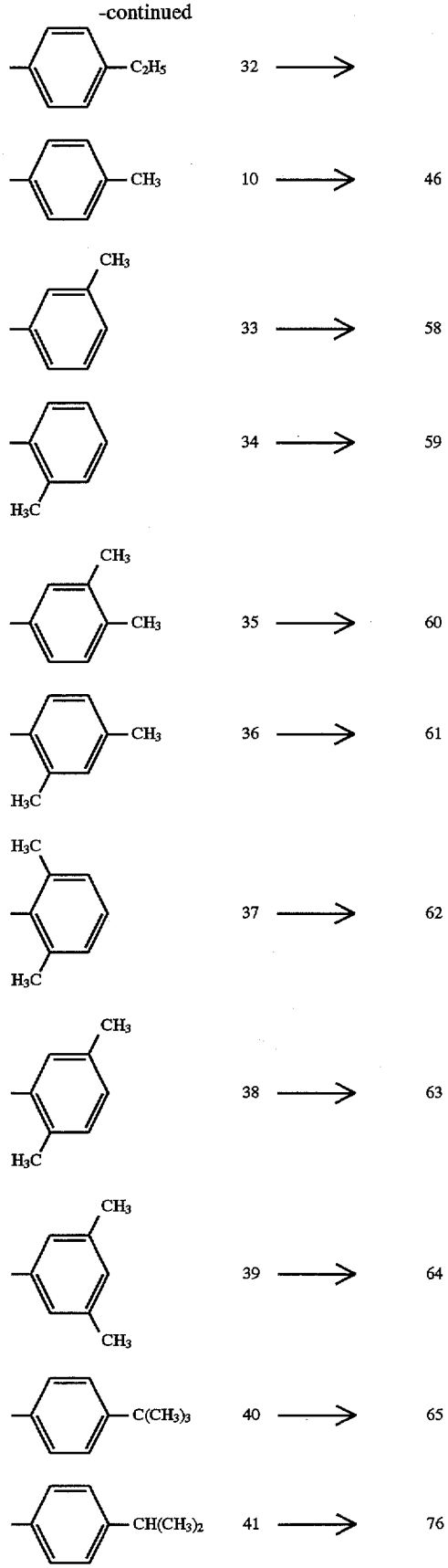

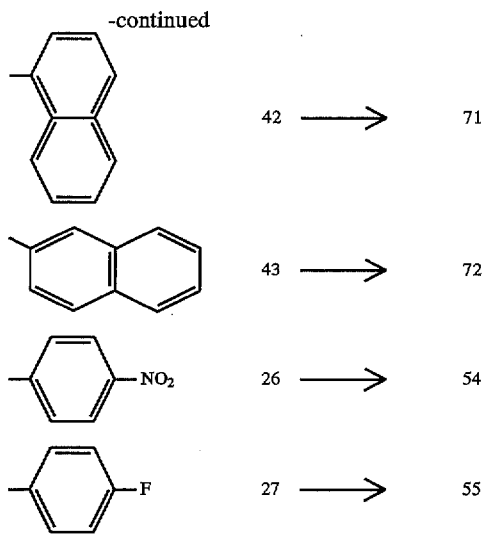

| | | |
|---|---|---|
| ![naphthyl] | 42 → | 71 |
| ![naphthyl2] | 43 → | 72 |
| -C6H4-NO2 | 26 → | 54 |
| -C6H4-F | 27 → | 55 |

Reaction Scheme A

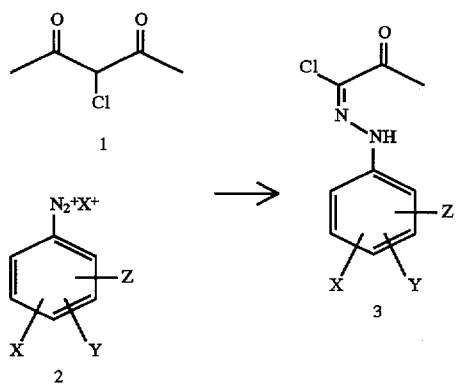

Reaction of commercially available 3-chloropentane-2,4-dione 1 with aryldiazonium salts 2 in the presence of a base such as aqueous sodium acetate gives chloroacetylhydrozone derivatives 3 with loss of acetic acid via an $S_E1$ type mechanism [Org. Reactions 10, 1-142 (1959); J. Am. Chem. Soc., 84, 143-178 (1979)]. The diazonium salts can be conveniently prepared by reacting arylamines with sodium nitrite in acid such as hydrochloric acid or directly with nitrosyl chloride [J. Org. Chem., 26, 5149, 2053 (1961); Org. Syn., 43, 12 (1963)]

Reaction Scheme B

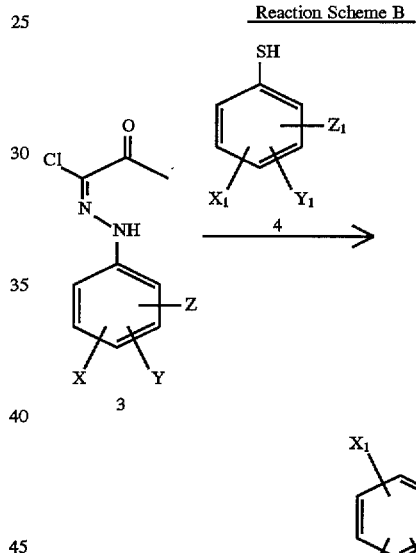

Reaction of chloroacetylhydrazone 3 with arylmercaptan 4 in the presence of a base such as triethylamine in a solvent such as DMF gives thioether 5. Alternatively, the sodium salt of the mercaptan can be prepared and added to 3 as referenced in Polish J. Chemistry 64, 741 (1990).

Reaction Scheme C

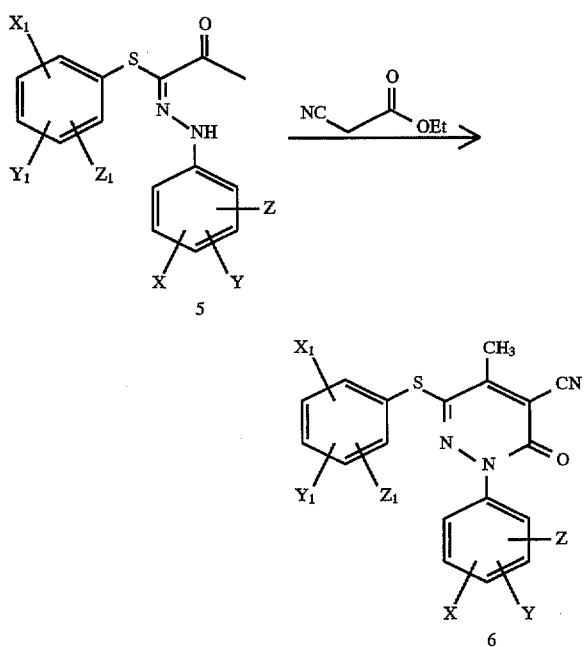

5

6

Reaction of compound 5 with ethylcyanoacetate under Knoevenagel conditions with ammonnium acetate produces pyridazinone analogs 6. The type of aromatic substitution may require forcing conditions at high temperates to achieve successful cyclization.

Sulfoxide derivatives 7a are prepared by reaction of compound 6 with 1.1 equivalents of m-chloroperbenzoic acid or with related oxidizing agents. Surfone derivatives 7 are prepared by reaction of compound 6 with 2.2 equivalents of m-chloroperbenzoic acid or with related oxidizing agents.

The compounds of Formula I in the present invention are also directed to a method for suppressing the immune system in a subject in need of such treatment comprising the administration to a subject in need of such treatment of a nontoxic immunosuppressant amount of Margatoxin. These compounds possess pharmacological activity such as immunosuppressive activity and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus,

REACTION SCHEME D

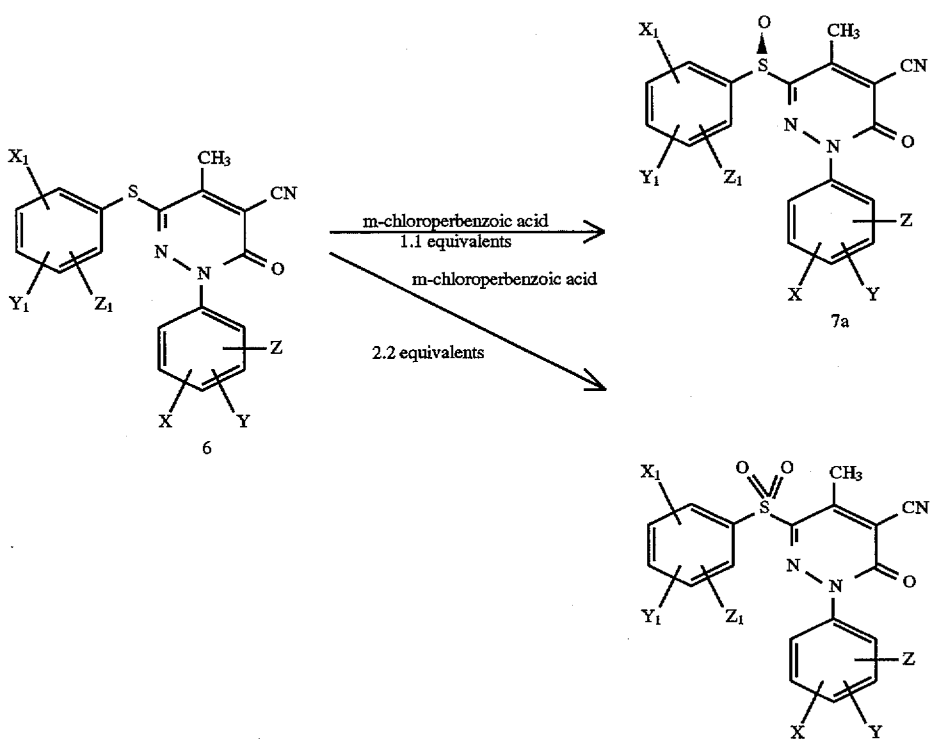

6

7a

7b

Pemphigus, bullous Pemphigoid, Epidermolysis bullosa, urticaria, angioedemas, vasculitides, erythemas, cutaneous eosinophilias, acne, Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratifis, herpetic keratitis, conical cornea, dystorphia epithelialis corneae, cornea leukoma, ocular pemphigus, Mooren's ulcer, Sclerifis, Graves' ophthalmopathy, severe intraocular inflammation, and the like.

The compounds of Formula I are also useful for preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/ allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations; in solid, semisolid, or liquid form, and in addition auxiliary, stabilizing, thickening and coloring agents and perfumes may be used.

For the treatment of these conditions and diseases caused by immmunoirregularity a compound of Formula I may be administered orally, topically, parenterally, by inhalation spray or rectally in dosage trait formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

The compounds of Formula I may optionally be employed in co-therapy with anti-proliferative agents. Particularly preferred is co-therapy with an antiproliferative agent selected from the group consisting of: azathioprine, brequinar sodium, deoxyspergualin, mizadbine, mycophenolic acid morpholino ester, cyclosporin, FK-506 and rapamycin.

Dosage levels of the compounds of the present invention are of the order from about 0.005 mg to about 10 mg per kilogram of body weight per day, preferably from about 0.005 mg to about 10 mg per kilogram of body weight per day, are useful in the treatment of the above-indicated conditions (from about 0.35 mg to about 700 mg per patient per day, assuming a 70 kg patient). In addition, the compounds of the present invention may be administered on an intermittent basis; i.e. at daily, semiweekly, weekly, semimonthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 1 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 10% by weight, preferably from 0.001 to 10% by weight, and most preferably from about 0.005 to 2% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

Preparation of 1-chloro-1-[(4-methoxyphenyl) hydrazono]-2-propanone

A vigorously stirred suspension of 16.75 g(0.136 mole) of 4-methoxyaminobenzene in 960 ml of 1N hydrochloric acid was cooled to 5° C. and treated, dropwise, with 15.8 g of sodium nitrite dissolved in 200 ml of water. The temperature was maintained at 5° C.+/−1° during the addition. After addition was complete, the reaction mixture was stirred in the cold for an additional 30 min. The pH of the reaction mixture was adjusted to 4.5 with solid sodium acetate (72 g). The resultant mixture was treated, dropwise, with 24 g (0.178 mole) of 3-chloro-2,4-pentanedione dissolved in 200 ml of methanol. After addition was complete, the reaction mixture was allowed to warm to room temperature over the next hour.

The suspension was extracted with 3–300 ml portions of ethyl ether. The combined extracts were washed with 4 volumes of water, dried over magnesium surf ate and filtered. The flitrate was evaporated in vacuo to yield 29 gm of a dark oil. The residue was dissolved in n-hexane:ethyl acetate (2:1) (approximately 400 ml) and the solution was passed over 1000 g of silica gel. Elution with n-hexane:ethyl acetate (3:1) yielded 11.66 g of 1-chloro-1-[(4-methoxyphenyl)hydrazono]-2-propanone, mp 114°–116° C. (hexane). A more preferred process for the production of 1-chloro-1-[(4-methoxyphenyl)hydrazono]-2-propanone is found in Example 85.

$^1$H NMR(400MHz, CDCl$_3$):2.53 (s,3H), 3.79 (s,3H) 6.89 (d, J=9Hz, 2H), 7.24 (d, J=9Hz, 2H), 8.36 (broad s,1H);

PBBI-NH3/CI-MS Calculated for C$_{10}$H$_{11}$ClN$_2$O$_2$(226.6); found: 227 (M+1), 123

EXAMPLE 2

Preparation of 1-chloro-1-[(4-phenoxyphenyl) hydrazono]-2-propanone

The reaction of 7.86(0.0424 mole) g of 4-phenoxyaminobenzene with 4.95 g of sodium nitrite and 7.5 g of 3-chloro-2,4-pentanedione as in Example 1 yielded 6.39 g of 1-chloro-1-[(4-phenoxyphenyl)hydrazono]-2-propanone, mp 108°–111° C.

$^1$H NMR(400MHz, CDCl$_3$): 2.54 (s,3H), 6.97 (m, 2H), 7.02 (d, J=10 Hz,2H), 7.07(m 1H), 7.21 (d, J=10 Hz, 2H), 7.31 (dd, J=16Hz, 8Hz, 2H), 8.41 (broad s,1H).

EXAMPLE 3

Preparation of 1-chloro-1-[[(4-methoxyphenoxy)-4-phenyl]hydrazono]-2-propanone a) Preparation of 4-(4-methoxyphenoxy)nitrobenzene A solution of 4-methoxyphenol (12.4 g, 0.10 mol) in 100 ml of dried dimethylforamide was treated, portionwise, with 4.0 g of 60% sodium hydride oil dispersion. The resultant solution was stirred at room temperature for 30 min. The solution was cooled and a solution of 4-fluoronitrobenzene (14.1 g, 0.10 mol) in 50 ml of dried dimethylformamide was added dropwise while keeping the temperature below 40° C. with external cooling. After addition was complete the reaction mixture was heated at 60° C. for 45 min when thin layer chromatography (6:1 hexane:ethyl acetate) show no starting material remaining. The reaction mixture was cooled, poured into 1500 ml of water and the resultant solids were collected by filtration. The crude 4-(4-methoxyphenoxy) nitrobenzene weighed 24.08 g and melted 100°–102.5° C.

$^1$H NMR(400MHz, CDCl$_3$): 3.81 (s, 3H) 6.92 (d, J=9Hz, 2H), 6.94 (d, J=9 Hz, 2H), 7.00 (d, J=9Hz, 2H), 8.15 (d, J=9 Hz, 2H).

b) Preparation of 4-(4-methoxyphenoxy)aminobenzene

A solution of the crude 4-(4-methoxyphenoxy) nitrobenzene (12.5 g 0.05 mol) dissolved in 300 ml of methanol containing 1.0 g of 10% palladium on carbon was reduced at 40 psi under a hydrogen atmosphere until uptake of hydrogen was complete. The catalyst was removed by filtration and the filtrate evaporated in vacuo to yield 10.4 g of 4-(4-methoxyphenoxy)aminobenzene, mp 70°–73° C.

$^1$H NMR(400MHz, CDCl$_3$): 3.76 (s, 3H), 6.65 (d, J=8.8 Hz, 2 H), 6.80 (m, 4H), 6.88 (d, J =9 Hz, 2H), 7.23 (broad s, 3H).

c) Preparation of 1-chloro-1-[[(4-methoxyphenoxy)-4-phenyl)hydrazono]-2-propanone The reaction of of 4-(4-methoxyphenoxy)aminobenzene with of sodium nitrite and 3-chloro-2,4-pentanedione as in Example 1 yielded 1-chloro-1-[[(4-methoxyphenoxy)-4-phenyl]hydrazonol-2-propanone.

EXAMPLE 4

Preparation of 1-chloro-1-[(4-nitrophenyl) hydrazono]-2-propanone

A warm solution of 8.33g (60.3 mmol) of 4-nitro-aminobenzene in 10 ml of glacial acetic acid was added to 100 ml of concentrated hydrochloric acid. The rapidly stirred resulting suspension was cooled to 5° C. and treated dropwise with 25 ml of water containing 4.99 g of sodium nitrite. The reaction mixture was stirred at 5° C. for an additional 30 rain after addition was complete. The diazonium solution was filtered in the cold. The cold diazonium filtrate was slowly added to a vigorously stirred suspension of 116 g of sodium acetate in 200 ml of a 50% aqueous methanol containing 10 g of 3-chloro-2,4-pentanedione. The reaction mixture was allowed to warm to room temperature and the yellow solids were collected by filtration. The crude product was washed with water and dried in vacuo at room temperature over phosphorus pentoxide. The product was recrystalized from ethanol to yield 9.12 g of 1-chloro-1-[(4-nitrophenyl)hydrazono]-2-propanone, mp 224°–226.5° C.

$^1$H NMR(400MHz, CDCl$_3$): 2.59 (s,3H),7.3 (d, J=9Hz, 2H), 8.26 (d, J=9Hz, 2H), 8.64 (broad s,1H).

EXAMPLE 5

Preparation of 1-chloro-1-[(3-methoxyphenyl) hydrazono]-2-propanone

The reaction of 13.96 g (113 mol) of 3-methoxyaminobenzene with 13.2g of sodium nitrite and 20 g of 3-chloro-2,4-pentane-dione as in Example 1 yields 13.3g of 1-chloro-1-[(3-methoxyphenyl) hydrazono]-2-propanone, mp 117°–119° C.

$^1$H NMR(400MHz, CDCl$_3$):2.54 (s,3H), 3.82 (s,3H), 6.61 (dd, J=8, 2 Hz, 1H), 6.76 (dd ,J=8, 2Hz, 1H), 6.80 (t, J=4.4 Hz, 1H), 7.24 (dd, J=8, 5 Hz, 1 H), 8.39 (broad s,1H)

EXAMPLE 6

Preparation of 1-chloro-1-[(4-methylsulfonylphenyl) hydrazono]-2-propanone a.) Preparation of 4-methylsulfonylnitrobenzene.

A solution of methyl 4-nitrophenylsulfide in 100 ml of methylene chloride was treated portion wise with 15.3 g of 80 % 3-chloroperoxybenzoic acid. The exothermic reaction was moderated by cooling in ice bath. The reaction mixture was stirred overnight at room temperature. The reaction mixture was diluted with an additional 500 ml of methylene chloride and washed with saturated aqueous sodium bicarbonate and the with 2 potions of water. The dried extracts were evaporated to yield the crude product. Recrystallization from ethanol yielded 5.5 g of 4-methylsulfonylnitrobenzene, mp 136°–139° C.

b ) Preparation of 4-methylsulfonylaminobenzene

A solution of 4-methylsulfonylnitmbenzene (4.9 g, 0.0243 mol) in 200 ml of methanol was reduced at 40 psi under a hydrogen atmosphere with 500 mg of 10% palladium on carbon until uptake of hydrogen was complete. The catalyst was removed by filtration and the filtrate was evaporated in vacuo to yield 4.08 g of 4-methylsulfonylaniline, mp 129°–131° C.

c) Preparation of 1-chloro-1-[(4-methylsulfonylphenyl)-hydrazono]-2-propanone

The reaction of 2.38 g of 4-methylsulfonylaminobenzene with 1.58 g of sodium nitrite and 2.4 g of 3-chloro-2,4-pentanedione as in Example 1 yielded 506 mg of 1-chloro-1-[(methylsulfonylphenyl) hydrazono]-2-propanone, mp 253°–255° C. (C$_6$H$_6$/hexane).

$^1$H NMR(400MHz, CDCl$_3$): 2.59 (s, 3H), 3.03 (s, 3H), 7.35 (d, J =9 Hz, 2H), 7.92 (d, J=9 Hz, 2H), 7.99 (d, J=9 Hz, 2H), 8.11 (d, J=9Hz, 2H), 8.57 (broad s, 1H).

EXAMPLE 7

Preparation of 1-chloro-1-[(3,4-methylenedioxyphenyl)hydrazono]-2-propanone a. The reaction of 1.9 g of 3,4-methylenedioxyaminobenzene with 1.58 g of sodium nitrite and 2.4 g of 3-chloro-2,4-pentanedione as in Example 1 yielded 2.24 g of crude 1-chloro-1-[(3,4-methylenedioxyphenyl)hydrazono]-2-propanone as a dark oil and was used without further purification.

EXAMPLE 8

Preparation of 1-chloro-1-[(4-methylthiophenyl) hydrazono]-2-propanone

The reaction of 5.7 g of 4-methylthioaminobenzene with 4.75 g of sodium nitrite and 7.22 g of 3-chloro-2,4-pentanedione in 60 ml of methanol as in Example 1 yielded 4.04 g of 1-chloro-1-[(4-methylthiophenyl)hydrazono]-2-propanone, mp 104°–107° C. (C$_6$H$_6$).

$^1$H NMR(400MHz, CDCl$_3$):2.46 (s, 3H), 2.54 (s, 3H), 7.15 (d, J=8.8 Hz, 2H), 7.27 (d, J=9 Hz, 2H), 8.39 (broad s, 1H).

EXAMPLE 9

Preparation of 1-chloro-1-[(4-t-butoxyphenyl) hydrazono]-2-propanone a) Preparation of 4-t-butoxynitrobenzene A solution of 12.4 (0.1 mol) g of solid potassium t-butoxide in 100 ml of dry dimethyl formamide was cooled and treated dropwise with a solution of 14.1 g (0.10 mol) of 4-flouronitrobenzene dissolved in 50 ml of dry dimethyl formamide. After addition was complete the reaction mixture was heated at 40 for 45 min. The reaction mixture was cooled and diluted with 1500 ml of water. The mixture was extracted with 3 portions of ether. The combined ether extracts were washed with 5 volumes of water, dried over magnesium sulfate and evaporated in vacuo. The residue was dissolved in 6:1 hexane-:ethyl acetate and chromatographed over 1000 g of silica gel. Elution with hexane ethyl acetate (6:1) yielded 16.9 g 4-t-butoxynitrobenzene as an oil.

$^1$H NMR(400MHz, CDCl$_3$): 2.98 (s, 9H), 6.74 (d, 8.4 Hz, 2H), 7.75 (d,8.4 Hz, 2H).

b) Preparation of 4-t-butoxyaminobenzene

A solution of 4-t-butoxynitrobenzene 8.49 g (0.043 mol) dissolved in 250 ml of methanol containing 1.0 g of 10 % palladium on carbon was reduced at 40 psi under a nitrogen atmosphere until the uptake of hydrogen was complete. The catalyst was removed by filtration and the filtrate was evaporated in vacuo to yield 6.9 g of 4-t-butoxyaminobenzene, mp 67°–69° C.

$^1$H NMR(400MHz, CDCl$_3$):1.26 (s, 9H), 6.57 (d, 8.4 Hz, 2H), 6.78 (d, 8.8 Hz, 2H)

c) Preparation of 1-chloro-1-[(4-t-butoxyphenyl) hydrazono]-2-propanone

The reaction of of 4-t-butoxyaminobenzene with sodium nitrite and 3-chloro-2,4-pentanedione as in Example 1 yields 1-chloro-1-[(4-t-butoxyphenyl)hydrazono]-2-propanone.

EXAMPLE 10

Preparation of 1-[(4-methylthiophenyl)thio]-1-[(4-methoxyphenyl)-hydrazono]-2-propanone A suspension of 31.7g (0,139 mol)of 1-chloro-1-[(4-methoxyphenyl)hydrazono]-2-propanone in 400 ml of ethanol was treated with 23.4 g of 4-methylthiothiophenol and 23.4 of triethylamine. The suspension was heated at reflux for 2 hours and cooled. The resultant suspension was filtered and the precipitate was washed with 1 portion of cold ethanol. The solids were dried in vacuo to yield 35.7 g of 1-[(4-methylthiophenyl)thio]-1-[(4-methoxyphenyl) hydrazono]-2-propanone, mp 124°–127° C.

$^1$H NMR(400MHz, CDCl$_3$): 2.41 (s, 3H), 2.54 (s, 3H), 3.78 (s, 3H), 6.87 (d, J=8.8 Hz, 2H), 7.12 (m, 6 H), 9.20 (broad s, 1H).

EXAMPLE 11

Preparation of 1-[(4-chlorophenyl)thio]-1-[(4-phenoxyphenyl)-ydrazono]-2-propanone The reaction of 600 mg g of 1-chloro-1-[(4-phenoxyphenyl)-hydrazono]-2-propanone with 344 mg of 4-chlorothiophenol and 336 ul of triethylamine in 6 ml of ethanol as Example 10 yielded 732 mg of 1-[(4-chlorophenyl)thio]-1-[(4-phenoxyphenyl)hydrazono]-2-propanone, mp 152°–155° C. (EtOH).

$^1$H NMR(400MHz, CDCl$_3$): 2.55 (s, 3H), 7.15 (m, 13 H), 9.23 (broad s, 1H).

EXAMPLE 12

Preparation of 1-[(4-chlorophenyl)thio]-1-[(4-methylthiophenyl)-hydrazono]-2-propanone The reaction of 500 mg (2.06 mmol) of 1-chloro-1-[(4-methylthiophenyl)hydrazono]-2-propanone with 304 mg of 4-chloro-thiophenol and 297 ul of triethylamine in 6 ml of ethanol as Example 10 yielded 446 g of 1-[(4-chlorophenyl)thio]-1-[(4-methylthiophenyl) hydrazono]-2-propanone, mp 98°–102° C.

$^1$H NMR(400MHz, CDCl$_3$): 2.46(s, 3H), 2.55(s, 3H), 7.13(d, J=8.8 Hz, 2H), 7.14(d, J=8.6 Hz, 2H), 7.20 (d, J=8.6 Hz, 2H), 7.26 (d, J=8.8 Hz, 2H), 9.21 (broad s, 1H).

EXAMPLE 13

Preparation of 1-[(4-chlorophenyl)thio]- 1-[(4-methoxy)phenoxy-phenyl)hydrazono]-2-propanone The reaction of 1-chloro-1-[(4-phenoxyphenyl) hydrazono]-2-propanone with 4-chlorothiophenol and triethylamine in ethanol as Example 10 yields 1-[(4-chlorophenyl)thio]-1-[(4-methoxy phenoxy) phenyl) hydrazono]-2-propanone.

EXAMPLE 14

Preparation of 1-[(4-chlorophenyl)thio]-1-[(4-nitrophenyl)hydrazono]-2-propanone The reaction of 2.47 g (10.2 mmol) of 1-chloro-1-[(4-nitrophenyl)hydrazono]-2-propanone with 1.72 g (18.0 mmol)of 4-chlorothiophenol as Example 10 yielded 3.19 g of 1-[(4-chlorophenyl) thio]-1- [(4-nitrophenyl)hydrazono]-2-propanone, mp 181°–183° C.

$^1$H NMR(400MHz, CDCl$_3$): 2.56 (s, 3H); 7.20 (d, J=8 Hz, 2H), 7.25 (d, J=8Hz, 2H), 7.28 (d, J=9 Hz, 2H), 8.24 (d, J=9 Hz, 2H), 9.38 (broad s, 1H).

EXAMPLE 15

Preparation of 1-[(4-chlorophenyl)thio]-1-[(3-methoxyphenyl)-hydrazono]-2-propanone The reaction of 2.88 g of 1 -chloro-1 -[(3-methoxyphenyl) -hydrazono]-2-propanone with 2.1 g of 4-chlorothiophenol and 2.04 ml of triethylamine in 35 ml of ethanol as Example 10 yielded 3.35 g of 1-[(4 -chlorophenyl)thio ]-1 -[(3- methoxyphenyl)hydrazono]-2-propanone, mp 107°–108.5° C.

$^1$H NMR(400MHz, CDCl$_3$): 2.55 (s, 3H), 3.81 (s, 3H), 6.61 (dd, J=9, 2 Hz, 1H), 6.74 (dd, J=9, 2 Hz, 1H), 6.81 (t, J=2 Hz, 1H), 7.14 (d, J=8.8 Hz, 2H), 7.20 (d, J=8.8 Hz, 2H), 7.21 (m, 2H), 9.20 (broad s, 1H).

EXAMPLE 16

Preparation of 1 -[(4-chlorophenyl)thio]-1 -[(4-t-butoxyphenyl)-hydrazono]-2-propanone The reaction of 1-chloro-1-[(4-t-butoxyphenyl) hydrazono]-2-propnone with 4-chlorothiophenol and triethylamine in ethanol as Example 10 yielded 1-[(4-chlorophenyl)thio]-1-[(4-t-butoxyphenyl)hydrazono]-2-propanone, mp 107-108.5° C.

EXAMPLE 17

Preparation of 1-[(3-chlorophenyl)thio]-1-[(4-methoxyphenyl)-hydrazono]-2-propanone The reaction of 468 mg (2.06 mmol) of 1-chloro-1-[(4-methoxyphenyl)hydrazono]-2-propanone, 344 mg of 3-chlorothiophenol and 336 ul of triethylamine in 6 ml of ethanol as in Example 10 yielded 689 mg of 1-[(3-chlorophenyl)thio]-1-[(4-methoxyphenyl)hydrazono]-2-propanone, mp 132°–134.5° C.

$^1$H NMR(400MHz, CDCl$_3$): 2.54 (s, 3H), 6.89 (d, J=9 Hz, 2 H), 7.0 (m, 1H), 7.14 (m, 3H), 7.17 (d, J=9H, 2H), 8.36 (broad s, 1H).

EXAMPLE 18

Preparation of 1-[(3,4-dichlorophenyl)thio]-1-[(4-methoxyphenyl)-hydrazono]-2-propanone The reaction of 468 mg (2.08 mmol) of 1-chloro-1-[(4-methoxyphenyl)hydrazono]-2-propanone, 427 mg (2.38 mmol) of 3, 4-dichlorothiophenol and 336 ul of triethylamine in 6 ml of ethanol as in Example 10 yielded 503 mg of 1-[(3,4-dichlorophenyl)thio]-1-[(4-methoxyphenyl) hydrazono]-2-propanone, mp 109°–113° C.

$^1$H NMR(400MHz, CDCl$_3$): 2.56 (s, 3H), 3.79 (s, 3H), 6.89 (d, J=9.0 Hz, 2H), 6.86 (dd, J=8.4, 2.2 Hz, 1 H), 7.18 (d, J=9 Hz, 2H), 7.26 (m 2H), 9.23 (broad S, 1H).

EXAMPLE 19

Preparation of 1-[(3,5-dichlorophenyl)thio]-1-[(4-methoxyphenyl)-hydrazono]-2-propanone The reaction of 387 mg (1.72 mmol) of 1-chloro-1-[(4-methoxyphenyl)hydrazono]-2-propanone, 350 mg (1.69 mmol) of 3,5-dichlorothiophenol and 279 ul of triethylamine in 4.5 ml of ethanol as in Example 10 yielded 385 mg of 1-[(3,5-dichlorophenyl)thio]-1-[(4-methoxyphenyl) hydrazono]-2-propanone, mp 168°–170° C.

$^1$H NMR(400MHz, CDCl$_3$): 2.58 (s, 3H), 3.79 (s, 3H), 6.90 (d, J=9.2 Hz, 2H), 7.00 (d, J=1.6 Hz, 2H), 7.14 (t, J=3.6 Hz, 1H), 7.19 (d, J=9.2 Hz, 2H), 9.23 (broad s, 1H).

PBBI-NH3/CI-MS Calculated for $C_{16}H_{14}C_2N_2O_2S(369)$; found: 369, 270 268

EXAMPLE 20

Preparation of 1-[(4-methoxyphenyl)thio]-1-[(4-methoxyphenyl)-hydrazono]-2-propanone The reaction of 780 mg (3.44 mmol) of 1-chloro-1-[(4-methoxyphenyl)hydrazono]-2-propanone, 570 mg (4.0 mmol) of 4-methoxythiophenol and 560 ul of triethylamine in 10 ml of ethanol as in Example 10 yielded 894 mg of 1-[(4-methoxyphenyl)thio]-1-[(4-methoxyphenyl) hydrazono]-2-propanone, mp 126°–128.5° C.

$^1$H NMR(400MHz, CDCl$_3$): 2.51 (s, 3H), 3.73 (s, 3H), 3.77 (s, 3H), 6.77 (d, J=8.8 Hz, 2H), 6.86 (d, 8.8 Hz, 2H), 7.11 (d, 8.8 Hz, 2H), 7.24 (d, 8.8, 2H), 9.23 (broad s, 1H).

EXAMPLE 21

Preparation of 1-[(3-methoxyphenyl)thio]-1-[(4-methoxyphenyl)-hydrazono]-2-propanone The reaction of 468 mg (2.08 mmol) of 1-chloro-1-[(4-methoxyphenyl)hydrazono]-2-propanone, 336 mg (2.38 mmol) of 3-methoxythiophenol and 560 ul of triethylamine in 10 ml of ethanol as in Example 11 yielded 536 mg of 1-[(3-methoxyphenyl)thio]-1-[(4-methoxyphenyl) hydrazono]-2-propanone, mp 97°–99° C.

$^1$H NMR(400MHZ, CDCl$_3$): 2.57 (s, 3H), 3.72 (d, 3H), 3.78 (d, 3H), 6.94 (m , 3H), 6.87 (d, J=9.2 Hz, 2H), 7.12 (d, J=8.8 Hz, 2H), 7.13 (m, 1H)

EXAMPLE 22

Preparation of 1-[(4-cyanophenyl)thio]-1-[(4-methoxyphenyl)-hydrazono]-2-propanone The reaction of 422 mg (1.86 retool) of 1-chloro-1-[(4-methoxyphenyl)hydrazono]-2-propanone, 290 mg (2.14 mmol) of 4-cyanothiophenol and 305 ul of triethylamine in 5.4 ml of ethanol as in Example 10 yielded 507 mg of 1-[(4-cyanophenyl)thio]-1-[(4-methoxyphenyl)hydrazono]-2-propanone, mp 182°–184° C.

$^1$H NMR(400MHz, CDCl$_3$) :2.59 (s, 3H), 3.79 (s, 3H), 6.89 (d, J=9 Hz,2H), 7.17 (d, J=9 Hz, 4H), 7.49 (d, J=9 Hz, 2H), 9.17 (broad s, 3H).

EXAMPLE 23

Preparation of 1-[(3,4-dimethoxyphenyl)thio]-1-[(,4-methoxyphenyl)-hydrazono]-2-propanone The reaction of 468 mg of 1-chloro-1 -[(4-methoxyphenyl)-hydrazono]-2-propanone, 404 mg of 3,4-dimethoxythiophenol and 336 ul of triethylamine in 6 ml of ethanol as in Example 10 yielded 632 mg of 1-[(3,4-dimethoxyphenyl)thio]-1 -[(4-methoxyphenyl)hydrazono]-2-propanone, mp 138°–141° C.

$^1$H NMR(400MHz, CDCl$_3$): 2.53 (s, 3H), 3.78 (s, 3H), 3.80 (s, 3H), 6.72 (d, J=8.4 Hz, 1H), 6.84 (m, 2H), 6.87 (d, J=9 Hz, 2H), 7.11 (d, J=9 Hz, 2H), 9.22 (broad S, 1H).

EXAMPLE 24

Preparation of 1-[(4-trifluoromethoxyphenyl)thio]-1-[(4-methoxyphenyl)-hydrazono]-2-propanone The reaction of 303 mg(1.34 mmol) of 1-chloro-1-[(4-methoxyphenyl)hydrazono]-2-propanone, 300 mg of 4-trifluoro-methoxythiophenol and 161 ul of triethylamine in 4.4 ml of ethanol as in Example 10. The solvent was removed in vacuo to yield the crude product. The residue was chromatographed of 100 g of silica gel to yield 355 mg of 1-[(4-trifuoromethoxyphenyl)thio]-1-[(4-methoxyphenyl)hydrazono]-2-propanone as a red oil.

$^1$H NMR(400MHz, CDCl$_3$): 2.56 (s, 3H), 3.79 (s, 3H), 6.89 (d, J=9 Hz, 2H), 7.08 (d, J=9 Hz, 2H), 7.16 (d, J=9 Hz, 2H), 7.20 (d, J=9 Hz, 2H).

PBBI-NH3/CI-MS Calculated for $C_{17}H_{15}F_3N_2O_3S(384)$; found: 385 (M+1), 284, 162

EXAMPLE 25

Preparation of 1-[(4-methylthiophenyl)thio]-1-[(4-methoxyphenyl)-hydrazono]-2-propanone The reaction of 486 mg (1.08 mmol) of 1-chloro-1-[(4-methoxyphenyl)hydrazono]-2-propanone, 371 mg of 4-methyl thiothiophenol and 336 ul of triethylamine in 6 ml of ethanol as in Example 10 to yield 582 mg of 1-[(4-methylthiophenyl)thio]-1-[(4-methoxyphenyl)hydrazono]-2-propanone, mp 124°–127° C.

$^1$H NMR(400MHz, CDCl$_3$): 2.41 (s, 3H), 2.54 (s, 3H), 3.78 (s, 3H), 6.87 (d, J=8.8 Hz, 2H), 7.12 (m, 6 H), 9.20 (broad s, 1H).

EXAMPLE 26

Preparation of 1-[(4-nitrophenyl)thio]-1-[(4-methoxyphenyl), hydrazono]-2-propanone The reaction of 936 mg (4.13 mmol) of 1-chloro-1-[(4-methoxyphenyl)hydrazono]-2-propanone ,736 mg of 4-nitrothiophenol and 672 ul of triethylamine in 12 ml of ethanol as in Example 10 yielded 1.19g of 1-[(4-nitrophenyl)thio]-1-[(4-methoxyphenyl)hydrazono]-2-propanone, mp 171°–175° C.

$^1$H NMR(400MHz, CDCl$_3$): 2.61 (s, 3H), 3.79 (s, 3H), 6.89 (d, J=9 Hz, 2H), 7.18 (d, J=9 Hz, 2 H), 7.23 (d, J=8.8 Hz, 2H), 8.07 (d, J=8.8 Hz, 2 H), 9.18 (broad s, 1 H).

EXAMPLE 27

Preparation of 1-[(4-fluorophenyl)thio]-1-[(4-methoxyphenyl)-hydrazono]-2-propanone The reaction of 780 mg (3.44 mmol) of 1-chloro-1 -[(4-methoxyphenyl)hydrazono]-2-propanone, 510 mg (3.98 mmol) of 4-fluorothiophenol and 560 ul of triethylamine in 10 ml of ethanol as in Example 10 yielded 975 mg of 1-[(4-fluorophenyl)thio]-1-[(4-methoxyphenyl)hydrazono]-2-propanone, mp 135°–137° C.

$^1$H NMR(400MHz, CDCl$_3$): 2.53 (s, 3H), 3.7 (s, 3H), 6.88 (d, J=9.2 Hz, 2H), 6.94 (t, J=17.2 Hz, 2 H), 7.14 (d, J=9.2 Hz, 2H), 7.22 (m, 2H), 9.24 (broad S, 1H).

EXAMPLE 28

Preparation of 1-[(4-methylsulfinylphenyl)thio]-1-[(4-methoxyphenyl)-hydrazono]-2-propanone a) Preparation of 0-4-methylthiophenyl dimethyl-thiocarbamate A solution of 250 ml of dry dimethylformamide containing 16 g (0.114 mol) methylmercaptophenol was treated portionwise with 4.56 g of 60% sodium hydride oil dispersion. After addition was complete the reaction mixture was stirred at room temperature for 45 min. Dimethylthiocarbamyl chloride (16.8 g, 0.136 mol) was added in one portion. After stirring at room temperature for 16 hr, the reaction mixture was poured into 1000 ml of water. The resultant mixture was extracted with 3 portions of ethyl acetate. The combined extracts were washed 4 times with saturated aqueous sodium chloride, dried over magnesium sulfate and filtered. The solvent was removed in vacuo to yield 26.8 g of crude product. Recrystallization from methanol yielded 19.9 of O-4-methylthiophenyl dimethylthiocarbamate, mp 92°–93° C.

b) Preparation of S-4-methylthiophenyl dimethyl- thiocarbamate

A solution of O-4-methylthiophenyl dimethylthiocarbamate (500 mg, 2.2 mmol) in 2 ml of tetramethylene sulfone under a nitrogen atmosphere was heated at 300° C. for 1 hour. The reaction mixture was cooled and passed over 50 g of silica gel. Elution with n-hexane:ethyl acetate (2: 1) yielded 345 mg of S-4-methylthiophenyl dimethylthiocarbamate, mp 98°–100° C.

c) Preparation of S-4-methylsulfinylphenyl dimethylthio-carbamate

A solution of S-4-methylthiophenyl-dimethylthiocarbamate, (2.0 g, 8.8 mmol) dissolved in 50 ml of methylene chloride was treated with a methylene chloride solution of 1.83 g of 80 % 3-chloroperoxybenzoic acid. The reaction mixture was stirred at room temperature for 2 hr. The reaction mixture was washed with a saturated aqueous sodium bicarbonate solution, dried over magnesium sulfate. The solvent was removed in vacuo to yield 2.06 g of S-4-methylthiophenyl dimethylthiocarbamate which was used without further purification.

d) Preparation of 4-methylsulfinylthiophenol

A. solution of N,N-dimethyl-4-methylsulfinylphenyl thiocarbamate 508 mg (2.1 mmol) was dissolved in 3 ml of methanol and treated with 4 ml of 10% aqueous sodium hydroxide. The reaction mixture was heated at reflux for 30 min. The solvent was removed in vacuo. The residue was diluted with water acidified with 2-N hydrochloric acid and extracted with ethyl acetate. The combined extracts were washed with brine, dried over magnesium sulfate and evaporated in vacuo to yield crude 4-methylsulfinylthiophenol.

e) Preparation of 1-[(4-methylsulfinylphenyl)thio]-1-[(4-methoxyphenyl)hydrazono]-2-propanone The reaction of 400 mg (1.76 mmol) of 1-chloro-1-[(4-methoxyphenyl)hydrazono]-2-propanone, 345 mg (2.0 mmol) of 4-methylsulfinylthiophenol and 287 ul of triethylamine in 6 ml of ethanol as in Example 10 yielded 238 mg of 1-[(4-methylsulfinylthiophenyl) thio]-1-[(4-methoxyphenyl)hydrazono]-2-propanone, mp 75°–80° C.

$^1$H NMR(400MHz, CDCl$_3$): 2.59 (s, 3H), 2.66 (s, 3H), 3.79 (s, 3H), 6.89 (d, J=9.2Hz, 2H), 7.17 (d, J=8.8 Hz, 2H), 7.27 (d, J=8.8 Hz, 2H), 7.49 (d, J=9.2 Hz, 2H), 9.25 (broad S, 1 H).

PBBI-NH$_3$/CI-MS Calculated for C$_{17}$H$_{18}$N$_2$O$_3$S$_2$ (362.4); found: 363 (M+1), 246

EXAMPLE 29

Preparation of 1-[(4-methylsulfonylphenyl)thio]-1-[(4-methoxyphenyl)-hydrazono]-2-propanone a) Preparation of S-4-(methylsulfonylphenyl dimethylthiocarbamate A solution of S-dimethyl-4-methylthiophenyl thiocarbamate (3.0 g, 13.2 mmol)(Example 296) dissolved in 30 ml of methylene chloride was treated with a methylene chloride solution of 5.49 g of 80% 3-chloroperoxybenzoic acid. The reaction mixture was stirred at room temperature for 3 hr. An additional 690 mg of 80% 3-chloroperoxybenzoic acid was added and the reaction mixture was stirred at room temperature for 16 hrs. The reaction mixture was washed with a saturated aqueous sodium bicarbonate solution, dried over magnesium sulfate. The solvent was removed in vacuo to yield 2.9 g of crude product. The residue was chromatographed over 200 g of silica gel. Elution with n-hexane:ethyl acetate (2:1) yielded 2.75 g of S-4-(methylsulfonylphenyl dimethylthiocarbamate PBBI-NH$_3$/CI-MS Calculated for C$_{10}$H$_{13}$NO$_3$S$_2$ (259.3); found: 260 (M+1), 174 b) Preparation of 4-methylsulfonylthiophenol

A solution of 2.75 g (10.6 mmol) of S-4-(methylsulfonylphenyl dimethylthiocarbamate was dissolved in 12 ml of methanol and treated with 20 ml of 10% aqueous sodium hydroxide. The reaction mixture was heated at reflux for 2 hr. The solvent was removed in vacuo. The residue was diluted with water, acidified with 2-N hydrochloric acid and extracted with ethyl acetate. The combined extracts were washed with brine, dried over magnesium sulfate and evaporated in vacuo to yield crude product. The residue was chromatograped over 100 g of silica gel. Elution with methylene chloride yielded 1.3 g of 4-methylsulfonylthiophenol, mp 54°–58° C.

c) Preparation of 1-[(4-methylsulfonylphenyl)thio]-1-[(4-methoxyphenyl)hydrazono]-2-propanone The reaction of 468 mg (2.06 mmol) of 1-chloro-1-[(4-methoxyphenyl)hydrazono]-2-propanone, 448 mg (2.38 mmol) of 4-methylsulfonylthiophenol and 336 ul of triethylamine in 6 ml of ethanol as in Example 1 yielded 670 mg of 1-[(4-methylsulfonylphenyl)thio]-1-[(4-methoxyphenyl) hydrazono]-2-propanone, mp 145°–153° C.

$^1$H NMR(400MHz, CDCl$_3$): 2.15 (s, 3H), 2.99 (s, 3H), 3.79 (s, 3H), 6.89 (d, J=8.8 Hz, 2H), 7.18 (d, J=8.8 Hz, 2H), 7.25 (d, J=8.8 Hz, 2H), 7.76 (d, J=8.8 Hz, 2H), 9.23 (broad s, 1H).

EXAMPLE 30

Preparation of 1-[(4-phenylphenyl)thio]-1-[(4-methoxyphenyl)-hydrazono]-2-propanone a) Preparation of 1-[(4-(phenyl)phenyl dimethylthiocarbamate The reaction of 2.5 g (14.6 mmol) of 4-phenylphenol with 587 mg of 60% sodium hydride and dimethyl thiocarbamyl chloride as in Example 29a yielded 925 mg of 4-phenylthiophenol thiocarbamate.

$^1$H NMR(400MHz, CDCl$_3$): 3.35 (s, 3H), 3.46 (s, 3H), 7.11 ( d, J=9 Hz, 2H), 7.32 (m, 1H), 7.41 (m, 2H), 7.59 (m, 4H).

PBBI-NH$_3$/CI-MS Calculated for C$_{15}$H$_{15}$NOS (257.3); found: 258 (M+1)

b) Preparation of S-4-(phenyl)phenyl dimethylthiocarbamate 4-phenylthiophenol thiocarbamate (900 mg, 3.5 mmol) was heated at 300° C. for 3 hr. The reaction mixture was cooled chromatographed over 100 g of silica gel. Elution with n-hexane:ethyl acetate (4:1) yielded 616 mg of rearranged product.

PBBI-NH$_3$/CI-MS Calculated for C$_{15}$H$_{15}$NOS (257.3); found: 258 (M+1)

c) Preparation of 4-phenylthiophenol

A solution of rearranged product (600 mg, 2.33 mmol) dissolved in 20 ml of tetrahydrofuran was treated with a methanolic solution of 200 mg of potassium hydroxide. The reaction mixture was stirred at room temperature for 16 hr. The reaction mixture was diluted with water and acidified with dilute hydrochloric acid. The resultant precipitate was collected by filtration, washed with water and dried at room temperature in vacuo to yield 4-phenylthiophenol, mp 92°–95° C.

d) Preparation of 1-[(4-phenylphenyl)thio ]-1 -[(4-methoxyphenyl)hydrazono]-2-propanone The reaction of 317 mg(1.4 mmol) of 1-chloro-1-[(4-methoxyphenyl)hydrazono]-2-propanone ,300 mg of 4-phenylthiophenol and 194 ul of triethylamine in 4.5 ml of ethanol as in Example 10 to yield 280 mg of 1-[(4-phenylphenyl)thio]-1-[(4-methoxyphenyl)hydrazono]-2-propanone, mp 115°–118° C.

$^1$H NMR(400MHz, CDCl3): 2.58 (s, 3H), 3.78 (s, 3H), 6.88 d, J=9 Hz, 2H), 7.25 (d, J=9 Hz, 2H), 7.44 (m, 9 H), 9.25 (broad s, 1H).

EXAMPLE 31

Preparation of 1-[(4-trifluoromethylphenyl)thio]-1-[(4-methoxyphenyl)-hydrazono]-2-propanone The reaction of 468 mg (2.06 mmol) of 1-chloro-1-[(4-methoxyphenyl)hydrazono]-2-propanone, 419 mg of 4-trifluoromethyl-thiophenol and 336 ul of triethylamine in 6 ml of ethanol as in Example 11 yielded 408 mg of 1-[(4-fluoromethylphenyl)thio]-1-[(4-methoxyphenyl) hydrazono]-2-propanone, mp 103°–104° C.

$^1$H NMR(400MHz, CDCl$_3$): 2.59 (s, 3H), 3.79 (s, 3H), 6.86 (d, J=9 Hz, 2H), 7.17 (d, J=9 Hz, 2H), 7.21 (d, J=8.4 Hz, 2 H), 7.46 (d, J=8.4 Hz, 2 H), 9.21 (broad s, 1H).

EXAMPLE 32

Preparation of 1-[(4-ethylphenyl)thio]-1-[(4-methoxyphenyl)-hydrazono]-2-propanone The reaction of 468 mg (2.06 mmol) of 1-chloro-1-[(4-methoxyphenyl)hydrazono]-2-propanone, 328 mg of 4-ethylthiophenol and 336 ul of triethylamine in 6 ml of ethanol as in Example 10 yielded 540 mg of 1-[(4-ethylphenyl)thio]-1-[(4-methoxyphenyl)hydrazono]-2-propanone, mp 106°–108° C.

¹H NMR(400MHz, CDCl₃): 1.15 (t, J=7.6 Hz, 3 H), 2.55 (s, 3H), 2.56 (m, 2H), 6.87 (d,J=9 Hz, 2H), 7.06 (d, J=9 Hz, 2H), 7.11 (d, J=8 Hz, 2H), 7.17 (d, J=8Hz, 2H), 9.21 (broad s,1H).

EXAMPLE 33

Preparation of 1-[(3-methylphenyl)thio]- 1-[(4-methoxyphenyl)-hydrazono]-2-propanone The reaction of 468 mg (2.06 mmol) of 1-chloro-1-[(4-methoxyphenyl)hydrazono]-2-propanone, 295 mg of 3-methylthiophenol and 336 ul of triethylamine in 6 ml of ethanol as in Example 10 yielded 543 mg of 1-[(3-methylphenyl)thiol-1-[(4-methoxyphenyl)hydrazono]-2-propanone, mp 141°–143.5° C.

¹H NMR(400MHz, CDCl₃): 2.25 (s, 3H), 2.56 (s, 3H), 3.78 (s, 3H), 6.85 (d, J=9 Hz, 2H), 6.98 (m, 3H), 7.14 (d J=9 Hz, 2H), 7.12 (m. 1H), 9.20 (broad s, 1H).

EXAMPLE 34

Preparation of 1-[(2-methylphenyl)thio]-1-[(4-methoxyphenyl)-hydrazono]-2-propanone The reaction of 468 mg (2.06 mmol) of 1-chloro-1-[(4-methoxyphenyl)hydrazono]-2-propanone, 295 mg (2.38 mmol) of 2-methylthiophenol and 336 ul of triethylamine in 6 ml of ethanol as in Example 10 yielded 418 mg of 1-[(2-methylphenyl)thio]-1-[(4-methoxyphenyl)hydrazono] -2-propanone, mp 112°–113.5° C.

¹H NMR(400MHz, CDCl₃): 2.45 (s, 3H), 2.57 (s, 3H), 3.77 (s, 3H), 6.86 (d, J=8.8 Hz, 2H), 7.03 (t, J=iH), 7.08 (m, 1H), 7.10(d, J=8.8 Hz, 2H), 7.16 (d, J=7.6 Hz, 1H), 9.05 (broad s, 1H).

EXAMPLE 35

Preparation of 1-[(3,4-dimethylthiophenyl)thio]-1-[(4-methoxyphenyl)-hydrazono]-2-propanone The reaction of 400 mg (1.77 mmol) of 1-chloro-1-[(4-methoxyphenyl)hydrazono]-2-propanone, 345 mg of 3,4-dimethyl-thiophenol and 2.87 ul of triethylamine in 6 ml of ethanol as in Example 10 yielded 238 mg of 1-[(3,4-dimethylphenyl)thio]-1-[(4-methoxyphenyl)hydrazono]-2-propanone, mp 138.5°–141° C.

¹H NMR(400MHz, CDCl₃): 2.16 (s, 3H), 2.54 (s, 3H), 3.78 (s, 3H), 6.87 (d, J=9 Hz, 2H), 6.97 (m , 3H), 7.12 (d, J=9 Hz, 2H), 9.22 (broad s, 1H).

EXAMPLE 36

Preparation of 1-[(2,4-dimethylthiophenyl)thio]-1-[(4-methoxyphenyl)-hydrazono]-2-propanone The reaction of 468 mg (2.08 mmol) of 1-chloro-1-[(4-methoxyphenyl)hydrazono]-2-propanone, 328 mg (2.38 mmol) of 2,4-dimethylthiophenol and 336 ul of triethylamine in 6 ml of ethanol as in Example 10 yielded 482 mg of 1-[(2,4-dimethylphenyl)thio]-1-[(4-methoxyphenyl)hydrazono]-2-propanone, mp 109°–111° C.

¹H NMR(400MHz, CDCl₃): 2.23 (s, 3H), 2.41 (s, 3H), 2.54 (s, 3H), 3.77 (s, 3H), 6.84 (broad s, 2H), 6.86 (d, J=9 .Hz, 2H), 6.99 (broad s, 1H), 7.08 (d, J=9 Hz, 2H), 9.04 (broad s, 1H).

EXAMPLE 37

Preparation of 1-[(2,6-dimethylthiophenyl)thio]-1-[(4-methoxyphenyl)-hydrazono]-2-propanone The reaction of 468 mg (2.08 mmol) of 1-chloro-1-[(4-methoxyphenyl)hydrazono]-2-propanone, 328 mg of 2,6-dimethyl-thiophenol and 336 ul of triethylamine in 6 ml of ethanol as in Example 10 yielded 462 mg of 1-[(2,6-dimethylphenyl)thio]-1-[(4-methoxyphenyl)hydrazono]-2-propanone, mp 107 °–109° C.

¹H NMR(400MHz, CDCl3): 2.44 (s, 6 H), 3.76 (s, 3H), 6.83 (d, J=8.8 Hz, 2H), 6.94 (d, J=8.8 Hz, 2H), 7.11 (m, 3H), 8.57 (broad s, 1H).

EXAMPLE 38

Preparation of 1 -[(2,5-dimethylphenyl)thio]-1 -[(4-methoxyphenyl)-hydrazono]-2-propanone The reaction of 468 mg (2.08 mmol) of 1-cbloro-1-[(4-methoxyphenyl)hydrazono]-2-propanone, 328 mg (2.38 mmol) of 2,5-dimethylthiophenol and 336 ul of triethylamine in 6 ml of ethanol as in Example 10 yielded 536 mg of 1-[(2,5-dimethylphenyl)thio]-1-[(4-methoxyphenyl) hydrazono]-2-propanone, mp 131°–133.5° C.

¹H NMR(400MHz, CDCl₃) 2.17 (s, 3H), 2.40 (s, 3H), 2.57 (s, 3 H), 6.71 (broad s, 1H), 6.89 (d, J=8.8 Hz, 2H), 6.89 (d, J=7.2 Hz, 1H), 7.04 (d, J=7.2 Hz, 1H), 7.09 (d, 8.8 Hz, 2H), 9.05 (broad s, 1H).

EXAMPLE 39

Preparation of 1 -[(3 ,5-dimethylphenyl)thio]-1-[(4-methoxyphenyl)-hydrazono]-2-propanone The reaction of 370 mg (1.46 retool) of 1-chloro-1-[(4-methoxyphenyl)hydrazono]-2-propanone, 260 mg (1.88 mmol) of 3,5-dimethylthiophenol and 271 ul of triethylamine in 4.3 ml of ethanol as in Example 10 yielded 310 mg of 1-[(3,5 -dimethylphenyl)thio]-1-[(4-methoxyphenyl) hydrazono]-2-propanone, mp 165°–167° C.

¹H NMR(400MHz, CDCl₃): 2.21 (s, 6H), 2.56 (s, 3H), 3.78 (s, 3H), 6.80 (m, 3H), 6.87 (d, J=9 Hz, 2H), 7.12 (d, J=9 Hz, 2H), 9.21 (braod s, 1H).

EXAMPLE 40

Preparation of 1-[(4-t-butyphenyl)thio]-1-[(4-methoxyphenyl)-hydrazono]-2-propanone The reaction of 780 mg (3.44 mmol) of 1-chloro-1-[(4-methoxyphenyl)hydrazono]-2-propanone, 665 mg (3.99 mmol) of 4-tert-butylthiophenol and 560 ul of triethylamine in 10 ml of ethanol as in Example 10 yielded 1.01g of 1-[(4-t-butylphenyl)thio]-1-[(4-methoxyphenyl)hydrazono] -2-propanone, mp 111°–113° C.

¹H NMR(400MHz, CDCl₃) 1.23 (s, 9H), 2.55 (s, 3H), 3.78 (s, 3H), 6.87 (d, J=8.8 Hz, 2 H)), 7.12 (d, J=8.8 Hz, 2H), 7.13 (d, J=8.8 Hz, 2 H), 7.24 (d, J=8.8 Hz, 2H), 9.25 (broad s, 1H).

EXAMPLE 41

Preparation of 1 -[(4-isopropylphenyl)thio]-1 -[(4-methoxyphenyl)-hydrazono]-2-propanone The reaction of 468 mg (1.08 mmol) of 1-chloro-1-[(4-methoxyphenyl)hydrazono]-2-propanone, 500 mg of 4-isopropyl-thiophenol and 336 ul of triethylamine in 10 ml of ethanol was heated at reflux for 2 hours. The reaction mixture was cooled and evaporated in vacuo. The residue was dissolved in 4:1 hexane: ethyl acetate and chromatographed over 100 g of silica gel. Elution with 4:1 hexane-:ethyl acetate yielded 221 mg of semi pure 1-[(4-isopropylphenyl)thio]-1-[(4-methoxyphenyl)hydrazono]-2-propanone, as a red oil.

¹H NMR(400MHz, CDCl₃): 1.16 (d, J=7.6 Hz, 6H), 2.42 (s, 3H), 2.80 (m, 1H), 3.76 (s, 3H), 6.86 (m, 4H), 7.11 (m, 4H), 9.23 (broad s, 1H).

EXAMPLE 42

Preparation of 1-[(1-napthyl)thio]-1-[(4-methoxyphenyl)hydrazono]-2-propanone

The reaction of 468 (2.02 mmol) mg of 1-chloro-1-[(4-methoxyphenyl)hydrazono]-2-propanone, 381 of 1-napthylenethiol and 336 ul of triethylamine in 6 ml of ethanol as in Example 10 yielded 510 mg of 1-[(4-isopropylphenyl)thio]-1-[(1-napthyl)hydrazono]-2-propanone, mp 130°–133° C.

¹H NMR(400MHz, CDCl₃): 2.59 (s, 3H), 3.75 (s, 3H), 6.81 (d, J=9 Hz, 2H), 7.0 (d, J=9 Hz, 2 H), 7.20 (m, 1H), 7.28 (m, 1H), 7.53(m, 1H), 7.60 (m, 1H), 7.70 (d, J=8.4 Hz, 1H), 7.84(d, J=8.4 Hz, 1H), 8.38 (d, J=8.4 Hz, 1H). 9.05 (broad s, 1H).

EXAMPLE 43

Preparation of 1-[(2-napthyl)thio]-1-[(4-methoxyphenyl)hydrazono]-2-propanone

The reaction of 468 (2.08 mmol) mg of 1-chloro-1-[(4-methoxyphenyl)hydrazono]-2-propanone, 381 of 2-napthylenethiol and 336 ul of triethylamine in 6 ml of ethanol as in Example 10 yielded 617 mg of 1-[(4-isopropylphenyl)thiol-1-[(2-napthyl)hydrazonol-2-propanone, mp 107°–110° C.

¹H NMR(400MHz, CDCl₃): 2.60 (s,3H), 3.77 (s, 3H), 6.86 (d, J=10 Hz2H), 7.12 (d, J -10 Hz, 2H), 7.25 (m, 1H), 7.41 (m, 2H), 7.69 (m, 5 H), 9.27 (broad s, 1H).

EXAMPLE 44

Preparation of 1-[(4-chlorophenyl)thio]-1-[(4-methylsulfonyl-phenyl)hydrazono]-2-propanone The reaction of 500 mg of 1-chloro-1-[(4-methylsulfonyl-phenyl-)hydrazono]-2-propanone, 304 mg of 4-chlorothiophenol and 297 ul of triethylamine in 6 ml of ethanol as in Example 10 yielded 419 mg of 1-[(4-chlorophenyl)thio]-1-[(4-methylsulfonylphenyl)hydrazono]-2-propanone.

¹H NMR(400MHz, CDCl₃): 2.56 (s, 3H), 3.03 (s, 3H), 7.18 (d, J=8.8 Hz, 2H), 7.23 (d, J=8.8 Hz, 2H), 7.33 (d, J=8.8 Hz, 2H), 7.90 (d, J=8.8 Hz, 2H), 9.33 (s, 3H).

EXAMPLE 45

Preparation of 1-[(4-chlorophenyl)thio]-1-[(3,4-methylenedioxyphenyl)-hydrazono]-2-propanone The reaction of 1.0 g of semi pure 1-chloro-1-[(3,4-methylenedioxyphenyl-)hydrazono]-2-propanone, 746 mg of 4-chlorothiophenol and 755 ul of triethylamine in 6 ml of ethanol as in Example 10 yielded 200 mg of 1-[(4-chlorophenyl)thio]-1-[(3,4-methylenedioxyphenyl)hydrazono]-2-propanone as a red oil.

¹H NMR(400MHz, CDCl₃): 2.54 (s, 3H), 5.55 (s, 2H), 6.53 (dd, J=8.3, 2 Hz, 1H), 6.74(d, J=8.2 Hz, 1H), 6.87 (d, J=2m, 1H), 7.12 (d, J=8.6 Hz, 2H), 7.20 (d, J=8.6 Hz, 2H), 9.17.(broad S, 1H).

EXAMPLE 46

Preparation of 6-[(4-methylphenyl)thio]-2,3-dihydro-2-(4-methoxyphenyl)-5-methyl-3-oxo-4-pyridazinecarbonitrile An intimate, magnetically stirred mixture of 440 mg (1.40 mmol) of 1-[(4-methylphenyl)thio]-1-[(4-methoxyphenyl) hydrazono]-2-propanone 370 ul of ethylcyanoacetate and 178 mg of ammonium acetate was heated under a nitrogen atmosphere at 160° C. for 30 min. The reaction mixture was cooled and dissolved in methylene chloride. The organic layer was washed successively with sat'd aqueous sodium bicarbonate and water. The organic layer was dried over magnesium sulfate and evaporated in vacuo to yield semi pure product. The residue was recrystallized from ethanol to yield yielded 342 mg of 6-[(4-methylphenyl)thio]-2,3-dihydro-2-(4-methoxyphenyl)-5-methyl -3 -oxo-4-pyridazinecarbonitrile, mp 148°–149° C.(EtOH).

¹H NMR(400MHz, CDCl₃) 2.35 (s, 3H), 2.52 (s, 3H), 3.78 (s, 3H), 6.82 (d, J=9.2 Hz, 2H), 7.18 (d, J=9.2 Hz, 2H), 7.34 (d, J=8 Hz, 2H), 7.36 (d, J=9.2 Hz, 2 H).

PBBI-NH₃/CI-MS Calculated for $C_{20}H_{17}N_3O_2S$ (363.4); Found: 364 (M+1), 339, 242, 124.

EXAMPLE 47

Preparation of 6-[(4-chlorophenyl)sulfinyl]-2,3-dihydro-2-(4-methoxyphenyl)-5-methyl-3-oxo-4-pyridazinecarbonitrile A solution of 100 mg (2.61 mmol) of 6-[(4-chlorophenyl)thio]-2,3-dihydro-2-(methoxyphenyl)-5-methyl-3-oxo-4-pyridazinecarbonitrile in 5 ml of methylene chloride was treated with 62 mg of 80% 3-chloroperoxybenzoic acid. The reaction mixture was stirred at room temperature for 16 hours. The solvent was removed in vacuo and the product was isolated by preparative thin layer chromatography. Elution with methylene chloride:2-propanol (100:2) yielded 70 mg of 6-[(4-chlorophenyl)sulfinyl]-2,3-dihydro-2-(methoxyphenyl)-5-methyl-3-oxo-4-pyridazinecarbonitrile, mp 161°–163° C.

¹H NMR(400MHz, CDCl₃): 2.57 (s,3H), 3.84(s,3H), 6.96 (d,J=9Hz, 2H), 7.47 (d, J=9Hz, 2H), 7.56 (dd, J=12, 8 Hz, 4H).

PBBI-NH3/CI-MS Calculated for $C_{19}H_{14}C_1N_{33}S$ (399.8) Found:400 (M+1), 394, 242,190.

EXAMPLE 48

Preparation of 6-[(4-chlorophenyl)sulfonyl]-2,3-dihydro-2-(4-methoxyphenyl)-5-methyl -3-oxo-4-pyridazinecarbonitrile A solution of 100 mg (2.61 mmol) of 6-[(4-chlorophenyl)-thio]-2,3-dihydro-2-(methoxyphenyl)-5-methyl-3-oxo-4-pyridazine-carbonitrile in 10 ml of methylene chloride was treated with 124 mg of 80% 3-chloroperoxybenzoic acid. The reaction mixture was stirred at room temperature for 16 hours. The solvent was removed in vacuo and the product was isolated by preparative thin layer chromatography. Elution with methylene chloride:2-propanol (100:2) yielded 60 mg of 6- [(4-chlorophenyl)sulfonyl]-2,3-dihydro-2-(methoxyphenyl)-5-methyl-3-oxo-4-pyridazinecarbonitrile, mp 175°–178° C.(EtOH).

¹H NMR(400MHz, CDCl₃): 2.88 (s, 3H), 3.80(s, 3H) 6.84 (d,J=9.2 Hz, 2H), 7.23 (d, J=9.2 Hz, 2H), 7.56 (d, J=8.8 Hz, 2H), 7.88 (d, J=8.8 m, 2H).

PBBI-NH₃/CI-MS Calculated for $C_{19}H_{14}C_1N_3O_4S$ (415.8); Found:416(M+1),242.

EXAMPLE 49

Preparation of 6-[(4-chlorophenyl)thio]-2,3-dihydro-2-(4-hydroxy-phenyl)-5-methyl-3-oxo-4-pyridazinecarbonitrile An intimate, magnetically stirred mixture of 2.5 g( 6.51 mmol) of 6-[(4-chlorophenyl)thio]-2,3 -dihydro-2-(4- methoxyphenyl)-5-methyl-3-oxo-4-pyridazinecarbornitrile and 7.7 g on dry pyridine hydrochloride under a nitrogen atmosphere was heated to 200° C. in an oil bath. The temperature was maintained for one hour. The reaction mixture was cooled and dissolved in methylene chloride. The organic solution was washed with brine. A precipitate resulted at the interface which was collected by filtration. recrystallization of the insoluble material from ethanol yielded 1.31 g of 6-[(4-chlorophenyl)thio]-2,3-dihydro-2-(4-hydroxyphenyl)-5-methyl-3-oxo-4-pyridazinecarbonitrile mp 261°–262.6° C. Evaporation of the dried organic layer and recrystallization of the residue from ethanol yielded an additional 107 mg of product.

$^1$H NMR(400MHz,CD$_3$OD): 2.54 (s, 3H), 6.75 (d, J=9Hz, H), 7.12 (d, J=9Hz, 2H), 7.4(d, J=9 Hz, 2H), 7.51 (d, J=9 Hz, 2H).

PBBI-NH$_3$/CI-MS Calculated for $C_{18}H_{12}C_1N_3O_2S$ (369.84); Found:370 (M+1), 178.

EXAMPLE 50

Preparation of 6-[(4-chlorophenyl)thio]-2,3-dihydro-2-(4-ethoxyphenyl)-5-methyl-3-oxo-4-pyridazinecarbonitrile A suspension of 100 mg (0.270 mmole) of 6-[(4-chlorophenyl)thio]-2,3-dihydro-2-(4-hydroxyphenyl)-5-methyl-3-oxo-4-pyridazinecarbonitrile in 5 ml of ethanol was treated successively with 42 mg of ethyl iodide (0.269 mmol) and 40 ul of 1,8-diazabicyclo[5.4.0]-undecane. The reaction mixture was heated at reflux for four hours. The solvent was removed in vacuo and the residue was chromatographed over silica gel. Elution with methylene chloride:isopropanol (100:2) yielded purified product, mp 138°–145° C.

$^1$H NMR(400MHz,CD$_3$OD):1.38 (t,3H), 4.04(q, 2H), 6.89 (d, J=9Hz,2H), 7.30 (d, J=9Hz, 2H), 7.42(d, J=9 Hz, 2H), 7.52(d, J=9 Hz, 2H);

PBBI-NH$_3$/CI-MS Calculated for $C_{20}H_{18}C_1N_3O_2S$ (399.8); Found:370 (M+1), 162.

EXAMPLE 51

Preparation of 6-[(3-chlorophenyl)thio]-2,3-dihydro-2-(4-methoxyphenyl)-5-methyl-3-oxo-4-pyridazinecarbonitrile The reaction of 361 mg of 1-[(3-chlorophenyl)thio]-1-[(4-methoxyphenyl)hydrazono]-2-propanone, 275 ul of ethylcyano acetate and 137 mg of ammonium acetate as in Example 46, yielded 268 mg of 6-[(3-chlorophenyl)thio]-2,3-dihydro -2-(4-methoxyphenyl)-5-methyl-3-oxo-4-pyridazinecarbonitrile, mp 123°–124.5° C. (EtOH).

$^1$H NMR(400MHz, CDCl$_3$): 2.53 (s, 3H), 3.79 (s, 3H), 6.85 (d, J=9.2 Hz, 2H), 7.33, (m, 3 H), 7.37 (d, J=9.2 Hz), 7.49 (t , J=7.2, 4 Hz, 1H).

PBBI-NH$_3$/CI-MS Calculated for $C_{19}H_{14}C_1N_3O_2S$ (383.8); Found:386, 384 (M+1) 242, 217, 194.

EXAMPLE 52

Preparation of 6-[(3,4-dichlorophenyl)thio]-2,3-dihydro-2-(4-methoxyphenyl)-5-methyl -3 -oxo-4-pyridazinecarbonitrile The reaction of 400 mg (1.08 mmol) of 1-[(3,4-dichlorophenyl)thio]-1-[(4-methoxyphenyl)hydrazono]-2-propanone, 275 ul of ethylcyano acetate and 137 mg of ammonium acetate as in Example 46, yielded 196 mg of 6-[(3, 4-dichlorophenyl)thio]-2,3-dihydro-2-(4-methoxyphenyl)-5 -methyl-3 -oxo-4-pyridazinecarbonitrile, mp 168°–171° C. (EtOH).

$^1$H NMR(400MHz, CDCl$_3$): 2.53 (s, 3H), 3.80 (s, 3H), 6.87 (d, J=8.8 Hz, 2H), 7.29 (d, J=8.4 Hz, 1H), 7.35 (d, J=8.8 Hz, 2 H), 7.45 (d, J=8.4 Hz, 1H), 7.60 (s, 1H).

PBBI-NH$_3$/CI-MS Calculated for $C_{19}H_{33}$ $C_{12}N_3O_2S$ (418.3); Found: 418(M+), 332, 242, 217, 207.

EXAMPLE 53

Preparation of 6-[(4-methoxyphenyl)thio]-2,3-dihydro-2-(4-methoxyphenyl)-5-methyl-3-oxo-4-pyridazinecarbonitrile The reaction of 463 mg (1.5 mmol) of 1-[(4-methoxyphenyl)thio]-1-[(4-methoxyphenyl)hydrazono]-2-propanone, 370 ul of ethylcyano acetate and 178 mg of ammonium acetate as in Example 46, yielded 126 mg of 6-[(4-methoxyphenyl)thio]-2,3-dihydro-2-(4-methoxyphenyl)-5 -methyl-3 -oxo-4-pyridazinecarbonitrile, mp 188°–190° C. (EtOH).

$^1$H NMR(400MHz, CDCl$_3$): 2.53 (s, 3H), 3.78 (s, 3H), 3.80 (s, 3H), 6.82 (d, J=9.2 Hz, 2H), 6.90 (d, J=8.8 Hz, 2H), 7.34 (d, J=9.2 Hz, 2H), 7.0 (d, J=8.8 Hz, 2H).

PBBI-NH$_3$/CI-MS Calculated for $C_{20}H_{17}N_3O_3S$ (379.4) Found:380 (M+1) 261,142, 147.

EXAMPLE 54

Preparation of 6-[(4-nitrophenyl)thio]-2,3-dihydro-2-(4-methoxyphenyl)-5-methyl-3-oxo-4-pyridazinecarbonitrile The reaction of 1.0 (1.5 mmol) mg of 1-[(4-nitrophenyl)-thio]-1-[(4-methoxyphenyl)hydrazono]-2-propanone, 739 ul of ethylcyano acetate and 368 mg of ammonium acetate as in Example 46, yielded 200 mg of 6-[(4-nitrophenyl)thio]-2,3-dihydro-2-(4-methoxyphenyl)-5-methyl-3-oxo-4-pyridazinecarbonitrile, mp 258°–260° C. (EtOH).

$^1$H NMR(400MHz, CDCl$_3$): 2.52 (s, 3 H), 3.80 (s, 3H), 6.87, (d, J=9.2 Hz, 2H), 7.36 (d, J=9.2 Hz, 2H), 7.52 (d, 8.4 Hz, 2H), 8.20 (d, J=8.8 Hz, 2 n).

PBBI-NH$_3$/CI-MS Calculated for $C_{19}H_{14}N_4O_4S$ (394) Found:395 (M+i), 365, 242, 215, 194

EXAMPLE 55

Preparation of 6-[(4-fluorophenyl)thio]-2,3-dihydro-2-(4-methoxyphenyl)-5-methyl-3-oxo-4-pyridazinecarbonitrile The reaction of 446 mg (1.40 mmol) of 1-[(4-fluorophenyl) thio]-1-[(4-methoxyphenyl)hydrazono]-2-propanone, 370 ethylcyano acetate and 178 mg of ammonium acetate as in Example 46, yielded 250 mg of 6-[(4-fluorophenyl)thio]-2,3-dihydro-2-(4-methoxyphenyl)-5-methyl-3-oxo-4-pyridazinecarbonitrile, mp 150.5°–152.5° C. (EtOH).

$^1$H NMR(400MHz, CDCl$_3$): 2.54 (s, 3H), 3.80 (s, 3H), 6.84(d, J=9.2 Hz, 2H), 7.34 (d, J=9.2 Hz, 2H), 7.58 (d, J=8.8 Hz, 2H), 7.65 (d, J=8.8 Hz, 2H).

PBBI-NH$_3$/CI-MS Calculated for $C_{19}H_{14}F_3N_3O_2S$ (367); Found: 368 (M+1),242.

EXAMPLE 56

Preparation of 6-[(4-trifluoromethylphenyl)thio]-2,3-dihydro-2-(4-methoxyphenyl)-5 -methyl-3-oxo-4-pyridazinecarbonitrile The reaction of 397 mg (1.08 mmol) of 1-[(4-trifluoromethylphenyl)thio]-1-[(4-methoxyphenyl)

hydrazono]-2-propanone, 275 ul of ethylcyano acetate and 136 mg of ammonium acetate as in Example 46, yielded 301 mg of 6-[(4-trifluoromethylphenyl)thio]-2,3-dihydro-2-(4-methoxyphenyl)-5-methyl-3-oxo-4-pyridazinecarbonitrile, mp 151°–155° C. (EtOH).

$^1$H NMR(400MHz, CDCl$_3$): 2.53 (s, 3H), 7.79 (s, 3H), 6.83 (d, J=8.8 Hz, 2H), 7.32 (d, J=8.8 Hz, 2H), 7.56 (d , J=8.4 Hz, 2H), 7.63 (d, J=8.4 Hz, 2 H).

PBBI-NH$_3$/CI-MS Calculated for C$_{20}$H$_{14}$F$_3$N$_3$O$_2$S (417.4); Found:418 (M+1), 242, 217, 194.

EXAMPLE 57

Preparation of 6-[(4-ethylphenyl)thio]-2,3-dihydro-2-(4-methoxyphenyl)-5-methyl-3-oxo-4-pyridazinecarbonitrile The reaction of 358 mg (1.08 mmol) of 1-[(4-ethylphenyl)-thio]-1-[(4-methoxyphenyl)hydrazono]-2-propanone, 275 ul of ethylcyano acetate and 136 mg of ammonium acetate as in Example 46 yielded 230 mg of 6-[(4-ethylphenyl)thio]-2,3-dihydro-2-(4-methoxyphenyl)-5-methyl-3 -oxo-4-pyridazinecarbonitrile, mp 159 -160° C. (EtOH).

$^1$H NMR(400MHz, CDCl$_3$): 2.55 (s, 3H), 3.74 (s, 3H), 6.74 (d, J=9.2 Hz, 2H), 7.33 (d, J=9.2Hz, 2H), 7.47 (m, 1H), 7.53 (m, 2H), 7.77 (m, 1H), 7.84 (m, 2H), 7.99 (s, 1H).

PBBI-NH$_3$/CI-MS Calculated for C$_{21}$H$_{19}$N$_3$O$_2$S (377.4); Found: 378 (M+i), 242, 217.

EXAMPLE 58

Preparation of 6-[(3-methylphenyl)thio]-2,3-dihydro-2-(4-methoxyphenyl)-5 -methyl-3 -oxo-4-pyridazinecarbonitrile The reaction of 339 mg (1.08 mmol) of 1-[(3-methylphenyl)thio]-1-[(4-methoxyphenyl)hydrazono]-2-propanone, 275 ul of ethylcyano acetate and 134 mg of ammonium acetate as in Example 46, yielded 125 mg of 6-[(3-methylphenyl)thio]-2,3-dihydro-2-(4-methoxyphenyl)-5-methyl-3 -oxo-4-pyridazinecarbonitrile, mp 121°–122.5° C. (EtOH).

$^1$H NMR(400MHz, CDCl$_3$): 2.33 (s, 3 H), 2.52 (s, 3H), 3.29 (s, 3H), 6.83 (d, J=9 Hz, 2H), 7.18 (m, 1H), 7.26 (m, 3H), 7.39 (d, J=9.2Hz, 2H).

PBBI-NH$_3$/CI-MS Calculated for C$_{20}$H$_{17}$N$_3$O$_2$S (363.44); Found: 364 (M+i), 242, 217, 194.

EXAMPLE 59

Preparation of 6-[(2-methylphenyl)thio]-2,3-dihydro-2-(4-methoxyphenyl)-5-methyl-3-oxo-4-pyridazinecarbonitrile The reaction of 339 mg (1.08 mmol) of 1 -[(2-methylphenyl)thio]-1-[(4-methoxyphenyl)hydrazono]-2-propanone, 275 ul of ethylcyano acetate and 134 mg of ammonium acetate as in Example 46, yielded 200 mg of 6-[(2-methylphenyl)thio]-2,3-dihydro-2-(4-methoxyphenyl)-5-methyl-3-oxo-4-pyridazinecarbonitrile, mp 144.5°–145.5° C. (EtOH).

$^1$H NMR(400MHz, CDCl$_3$): 2.38 (s, 3H), 2.55 (s, 3H), 3.77 (s, 3H), 6.77 (d, J=9.2 Hz, 2H), 7.20 (m, 1H), 7.29 (d, J=9.2 Hz, 2H), 7.31 (m, 1H), 7.41 (d, J=7.2 Hz, 1H).

PBBI-NH$_3$/CI-MS Calculated for C$_{20}$H$_{17}$N$_3$O$_2$S (363.44); Found:364 (M+1)

EXAMPLE 60

Preparation of 6-[(3,4-dimethylphenyl)thio]-2,3-dihydro-2-(4-methoxyphenyl)-5-methyl-3-oxo-4-pyridazinecarbonitrile The reaction of 355 mg (1.08 mmol) of 1-[(3,4-dimethylphenyl)thio]-1-[(4-methoxyphenyl)hydrazono]-2-propanone, 275 ul of ethylcyano acetate and 134 mg of ammonium acetate as in Example 46, yielded 250 mg of 6-[(3, 4-dimethylphenyl)thio]-2,3-dihydro-2-(4-methoxyphenyl)-5-methyl-3-oxo-4-pyridazinecarbonitrile, mp 158°–160° C. (EtOH).

$^1$H NMR(400MHz, CDCl$_3$): 2.24 (s, 3H), 2.26 (s, 3H), 2.53 (s, 3H), 3.80 (s, 3H), 6.84 (d, J=9 Hz, 2H), 7.28 (m, 3H), 7.40 (d, J=9 Hz, 2H).

PBBI-NH$_3$/CI-MS Calculated for C$_{21}$H$_{19}$N$_3$O$_2$S (377.46) Found: 378 (M+1), 242, 217, 194.

EXAMPLE 61

Preparation of 6-[(2,4-dimethylphenyl)thio]-2,3-dihydro-2-(4-methoxyphenyl)-5-methyl-3-oxo-4-pyridazinecarbonitrile The reaction of 355 mg of 1-[(2,4-dimethylphenyl)thio]-1-[(4-methoxyphenyl)hydrazono]-2-propanone, 275 ul of ethylcyano acetate and 134 mg of ammonium acetate as in Example 46, yielded 223 mg of 6-[(2,4-dimethylphenyl)thio]-2,3-dihydro-2-(4-methoxyphenyl)-5-methyl-3-oxo-4-pyridazinecarbonitrile, mp 166°–168.5° C. (EtOH).

$^1$H NMR(400MHz, CDCl$_3$): 2.32 (s, 3H), 3.34 (s, 3h), 3.77 (s, 3H), 6.78 (d, J=9.2 Hz, 2H), 7.00 (broad d, J=9.2 Hz, 1H), 7.10 (broad S, 1H), 7.30 (d, J=9.2 Hz, 2H).

PBBI-NH$_3$/CI-MS Calculated for C$_2$IH$_{19}$ N$_3$O$_2$S (377.46); Found:378 (M+1)

EXAMPLE 62

Preparation of 6-[(2,6-dimethylphenyl)thio ]-2,3-dihydro-2-(4-methoxyphenyl)-5-methyl-3-oxo-4-pyridazinecarbonitrile The reaction of 355 mg (1.08 mmol) of 1-[(2,6-dimethylphenyl)thio]-1-[(4-methoxyphenyl)hydrazono]-2-propanone, 275 ul of ethylcyano acetate and 134 mg of ammonium acetate as in Example 46, yielded 195 mg of 6-[(2,6 dimethylphenyl)thio]-2,3-dihydro-2-(4-methoxyphenyl)-5-methyl-3-oxo-4-pyridazinecarbonitrile ,top 221°–224° C. (EtOH)

1H NMR(400MHz, CDCl$_3$): 2.39 (s, 6H), 2.61 (s, 3H), 3.75(s, 3H), 6.7 (d, J=9.2 Hz, 2 Hz), 7.14 (d, J=7.2 Hz, 2H), 7.23 (m, 3H).

PBBI-NH$_3$/CI-MS Calculated for C$_{21}$H$_{19}$ N$_3$O$_2$S (377.46)( ); Found:378 (M+1)

EXAMPLE 63

Preparation of 6-[(2,5-dimethylphenyl)thio]-2,3-dihydro-2-(4-methoxyphenyl)-5-methyl-3 -oxo-4-pyridazinecarbonitrile The reaction of 355 mg of 1-[(2,5-dimethylphenyl)thio]-1-[(4-methoxyphenyl)hydrazono]-2-propanone, 275 ul of ethylcyano acetate and 134 mg of ammonium acetate as in Example 46, yielded 215 mg of 6-[(2,5 -dimethylphenyl)thio]-2,3-dihydro-2-(4-methoxyphenyl)-5-methyl-3-oxo-4-pyridazinecarbonitrile, mp 140°–142° C.(EtOH).

$^1$H NMR(400MHz, CDCl$_3$): 2.84 (s, 3H), 2.33 (s, 3H), 3.77 (s, 3 H), 6.79 (d, J=9.2 Hz, 2 H), 7.11 (broad d, J=8 Hz, 2 H), 7,.17 (d, J=8 Hz, 2 H), 7.33 (d, J=9.2 Hz, 2H).

PBBI-NH$_3$/CI-MS Calculated for C$_2$IH$_{19}$ N$_3$O$_2$S (377.46); Found: 378 (M+1)

EXAMPLE 64

Preparation of 6-[(3,5-dimethylphenyl)thio]-2,3-dihydro-2-(4-methoxyphenyl)-5-methyl-3-oxo-4-pyridazinecarbonitrile The reaction of 310 mg (0.945 mmol) of 1-[(3,5-dimethylphenyl)thio]-1-[(4-methoxyphenyl)hydrazono]-2- propanone, 240 ul of ethylcyano acetate and 80 mg of ammonium acetate as in Example 46, yielded 155 mg of 6-[(3,5-dimethylphenyl)thio]-2,3-dihydro-2-(4-methoxyphenyl)-5-methyl-3 -oxo-4-pyridazinecarbonitrile, mp 175°–177° C.(HOAc).

1H NMR(400MHz, CDCl$_3$): 2.29 (s, 6H), 2.51 (s, 3H), 3.80 (s, 3H), 6.84 (d, J=9.2 Hz, 2H), 6.99 (s, 1H), 7.07 (s, 1H), 7.42 (d, J=8.8 Hz, 2H).

PBBI-NH$_3$/CI-MS Calculated for C$_{21}$H$_{19}$ N$_3$O$_2$S (377.46); Found:378 (M+1), 220, 163

EXAMPLE 65

Preparation of 6-[(4-tert-butylphenyl)thio]-2,3-dihydro-2-(4-methoxyphenyl)-5 -methyl-3 -oxo-4-pyridazinecarbonitrile The reaction of 552 mg (1.39 mmol) of 1-[(4-tert-butylphenyl)thio]-1-[(4-methoxyphenyl)hydrazono]-2-propanone, 370 ul of ethylcyano acetate and 178 mg of ammonium acetate as in Example 45 yielded 380 mg of 6-[(4-tert-butylphenyl)thio]-2,3-dihydro-2-(4-methoxyphenyl)-5 -methyl-3 -oxo-4-pyridazinecarbonitrile, mp 186°–188° C. EtOH).

$^1$H NMR(400MHz,CDCl$_3$: 1.31 (s, 3H),.2.53 (s, 3H), 3.77 (s, 3H), 6.78 (d, 9.2 Hz, 2H), 7.30 (d, 9.2 Hz, 2H), 7.40 (broad s, 4H).

PBBI-NH$_3$/CI-MS Calculated for C$_{23}$H$_{23}$N$_3$O$_2$S (405.5); Found: 405 (M+), 244, 217, 151.

EXAMPLE 66

Preparation of 6-[(3,5-dichlorophenyl)thio]-2,3-dihydro-2-(4-methoxyphenyl)5-methyl-3 -oxo-4-pyridazinecarbonitrile The reaction of 385 mg (0.923 mmol) of 1-[(3,5-dichlorophenyl)thio]-1-[4-methoxyphenyl)hydrazono]-2-propanone, 236 ul of ethylcyano acetate and 78 mg of ammonium acetate as in Example 45, yielded 205 mg of 6-[(3,5-dichlorophenyl)thio]-2,3-dihydro-2-(4-methoxyphenyl)5-methyl-3-oxo-4-pyridazinecarbonitrile, mp 195°–197° C. (HOAc).

$^1$H NMR(400 MHz, DMSO-d$_6$): 2.43 (s, 3H), 3.78 (2, 3H), 7.01 (d, J=9 Hz, 2H), 7.40 (d, J=9 Hz, 2H), 7.59 (d, 1 -2Hz, 1H), 7.64 (d, J=2Hz, 2H).

EXAMPLE 67

Preparation of 6-[(3-methoxyphenyl)thio]-2,3-dihydro-2-(4-methoxyphenyl)5-methyl-3 -oxo4-pyridazinecarbonitrile The reaction of 356 mg (1.08 mmol) of 1-[(3-methoxyphenyl)thio]-1-[4-methoxyphenyl)hydrazono]-2-propanone, 275 ul of ethylcyano acetate and 137 mg of ammonium acetate as in Example 46, yielded 230 mg of 6-[(3-methoxyphenyl)thio]-2,3-dihydro-2-(4-methoxyphenyl)5-methyl-3-oxo-4-pyridazinecarbonitrile, mp 143°–144.5° C. (EtOH).

$^1$H NMR(400 MHz, CDCl$_3$): 2.51(s, 3H), 3.76 (s, 3H), 3.79 (s, 3H), 6.84 (d, J=9.2Hz, 2H), 6.90 (dd, J=8.8,2 Hz, 1H), 6.99 (m, 2H), 7.28 (t, J=8.8 Hz, 1H), 7.40 (d, J=9.2 Hz, 2H).

PBBI-NH$_3$/CI-MS Calculated for C$_{20}$H$_{17}$N$_3$O$_3$S (379.4) Found 380 (M+1)

EXAMPLE 68

Preparation of 6-[(3,4-dimethoxyphenyl)thio]-2,3-dihydro-2-(4-methoxyphenyl)5-methyl-3-oxo4-pyridazinecarbonitrile The reaction of 388 mg(1.08 mmol) of 1-[(3,5-dimethoxyphenyl)thio]-1-[4-methoxyphenyl)hydrazono]-2-propanone, 275 ul of ethylcyano acetate and 137 mg of ammonium acetate as in Example 46, yielded 158 mg of 6-[(3,5-dimethoxyphenyl)thio]-2,3-dihydro-2-(4-methoxyphenyl)5-methyl-3-oxo -4-pyridazinecarbonitrile, mp 181°–184° C.(EtOH).

$^1$H NMR(400 MHz, CDCl$_3$): 3.78 (s, 3H), 3.81 (s, 3H) 3.88 (s, 3H), 6.81 (d, 9.2 Hz, 2H), 6.85 (d, J=8.3 Hz, 1H), 7.00 (d, 2Hz, 1H), 7.07 (dd, J=8.3, 2 Hz, 1H), 7.36 (d, J=9.2 Hz, 2H).

PBBI-NH$_3$/CI-MS Calculated for C$_{21}$H$_{19}$N$_3$O$_4$S (409.4), Found 410 (M+1)

EXAMPLE 69

Preparation of 6-[(4-trifluoromethoxyphenyl)thio]-2,3-dihydro-2-(4 -methoxyphenyl)5-methyl-3-oxo-4-pyridazinecarbonitrile The reaction of 290 mg (0.823 mmol) of 1-[(4-trifluoromethoxyphenyl)thio]-1 -[4-methoxyphenyl) hydrazono]-2-propanone, 210 ul of g of ethylcyano acetate and 69 mg of ammonium acetate as in Example 46, yielded 85 mg of 6-[(4-trifluoromethoxyphenyl)thio]-2,3-dihydro-2-(4-methoxyphenyl) 5-methyl-3-oxo-4-pyridazinecarbonitrile, mp 165°–167° C.(EtOH).

$^1$H NMR(400 MHz, CDCl$_3$): 2.55 (s, 3H), 3.78 (s, 3H), 6.80 (d, J=9.2 Hz, 2H), 7.24 (d, J=8.8 Hz, 2H), 7.30 (d, J=9.2 Hz, 2H), 7.53 (d, J=8.8 Hz, 2H),.

PBBI-NH$_3$/CI-MS Calculated for C$_{20}$H$_{14}$F$_3$N$_3$O$_3$S (433.4); Found 434 (M+1)

EXAMPLE 70

Preparation of 6-[(4-cyanophenyl)thio]-2,3-dihydro-2-(4-methoxyphenyl)5-methyl-3 -oxo-4-pyridazinecarbonitrile The reaction of 507 mg (1.56 mmol) of 1-[(4-cyanophenyl) thio]-1-[4-methoxyphenyl)hydrazono]-2-propanone, 400 ul of ethylcyano acetate and 194 mg of ammonium acetate as in Example 45, yielded 42 mg of 6-[(4-cyanophenyl)thio]-2,3-dihydro-2-(4-methoxyphenyl) 5-methyl-3-oxo-4-pyridazinecarbonitrile, mp 195°–198° C. (HOAc).

$^1$H NMR(400 MHz, DMSO-d$_6$): 2.41 (s, 3H), 3.78 (s, 3H), 7.02 (d, J=9.2 Hz, 2H), 7.42 (d, J=9.2 Hz, 2H), 7.63 (d, J=8.4 Hz, 2H), 7.82 (d, J=8.4 Hz, 2H).

PBBI-NH$_3$/CI-MS Calculated for C$_{20}$H$_{14}$N$_4$O$_2$S (374.4); Found 375 (M+1)

EXAMPLE 71

Preparation of 6-[(1-naphthyl)thio]-2,3-dihydro-2-(4-methoxyphenyl)5-methyl -3-oxo -4-pyridazinecarbonitrile The reaction of 378 mg(1.08 mmol) of 1-[(1-napthyl)thio] -1- [4-methoxyphenyl)hydrazono]-2-propanone, 275 ul of ethylcyano acetate and 137 mg of ammonium acetate as in Example 46, yielded 205 mg of 6-[(1 -napthyl)thio]-2,3 -dihydro-2-(4-methoxyphenyl) 5-methyl-3 -oxo-4-pyridazinecarbonitrile, mp 181°–183° C. EtOH)

$^1$H NMR(400 MHz, CDCl$_3$): 2.63 (s, 3H), 3.69 (s, 3H), 6.56 (d, J=9.2 Hz, 2H), 6.84 (d, J=9.2 Hz, 2H), 7.44 (t, J=8, 8 Hz, 1H), 7.57 (m, 2H). 7.76 (d, J=6.4 Hz, 1H), 7.92 (m, 2H), 8.21 (m, 1H).

PBBI-NH$_3$/CI-MS Calculated for C$_{23}$H$_{17}$N$_3$O$_2$S (399.4) Found 400 (M+1)

EXAMPLE 72

Preparation of 6-[(2-napthyl)thio]-2,3-dihydro-2-(4-methoxyphenyl)5-methyl-3 -oxo-4-pyridazinecarbonitrile The reaction of 378 mg (1.08 mmol) of 1-[(2-napthyl)thio]-1-[4-methoxyphenyl)hydrazono]-2-propanone, 275 ul of ethylcyano acetate and 134 mg of ammonium acetate as in Example 46 yielded 155 mg of 6- [(2-napthyl)thio]-2,3-dihydro-2-(4-methoxyphenyl)5-methyl-3-oxo-4-pyridazinecarbonitrile, mp 169°–170° C. (EtOH).

$^1$H NMR(400 MHz, CDCl3): 2.55 (s, 3H), 3.74 (s, 3H), 6.74 (d, J=9.2 Hz, 2H), 7.33 (d, J=9.2 Hz, 2H), 7.47 (m 1H), 7.53 (m, 2H), 7.79 (m, 1H), 7.83 (d, J=8.8 Hz, 2 H), 7.99 (broad s, 1H).

PBBI-NH$_3$/CI-MS Calculated for $C_{23}H_{17}N_3O_2S$ (399.4); Found: 400 (M+i), 242, 217, 194, 160.

EXAMPLE 73

Preparation of 6-[(4-methylthiophenyl)thio]-2,3-dihydro-2-(4-methoxyphenyl)5-methyl-3-oxo-4-pyridazinecarbonitrile The reaction of 373 mg (1.08 mmol) of 1-[(4-methylthiophenyl)thio]-1-[4-methoxyphenyl)hydrazono]-2-propanone, 275 ul of ethylcyano acetate and 136 mg of ammonium acetate as in Example 46, yielded 135 mg of 6-[(methylthiophenyl)thio]-2,3-dihydro-2-(4-methoxyphenyl)5-methyl-3-oxo-4-pyridazinecarbonitrile, mp 155°–157° C. (EtOH).

$^1$H NMR(400 MHz, CDCl$_3$): 2.47 (s. 3H), 2.53(s, 3H), 3.79 (s, 2H), 6.83 (d, J=9 Hz, 2H), 7.22 (d, 9 Hz, 2H), 7.35 (d, J=7 Hz, 2h), 7.27

PBBI-NH$_3$/CI-MS Calculated for $C_{20}H_{17}N_3O_2S_2$ (395.5); Found 396 (M+1).

EXAMPLE 74

Preparation of 6-[(4-methylsulfinylphenyl)thio]-2,3-dihydro-2-(4-methoxyphenyl)5 -methyl-3 -oxo-4-pyridazinecarbonitrile The reaction of 238 mg (0.657 mmol) of 1-[(methylsulfinylphenyl)thio]-1-[4-methoxyphenyl)hydrazono]-2-propanone, 167 ul of ethylcyano acetate and 83 mg of ammonium acetate as in Example 46, yielded 75 mg of 6-[(4-methylsulfinylphenyl)thio]-2,3-dihydro-2-(4-methoxyphenyl)5-methyl-3-oxo-4-pyridazinecarbonitrile, mp 176°–178° C.

$^1$H NMR(400 MHz, CDCl$_3$): 2.55 (s, 3H), 2.71 (s, 3H), 3.79 (s, 3H), 6.83 (d, J=9.2 Hz, 2H), 7.33 (d, J=9.2 Hz, 2H), 7.61 (d, J=8.8 Hz, 2H), 7.64 (d, J=8.8 Hz, 2H).

PBBI-NH$_3$/CI-MS Calculated for $C_{20}H_{17}N_3O_3S_2$ (411); Found 412 (M+1)

EXAMPLE 75

Preparation of 6-[(4-methylsulfonylphenyl)thio]-2,3-dihydro-2-(4-methoxyphenyl)5-methyl-3-oxo-4-pyridazinecarbonitrile The reaction of 408 mg (1.08 mmol) of 1-[(4-methylsulfonylphenyl)thio]-1-[4-methoxyphenyl)hydrazono]-2-propanone, 275 ul of ethylcyano acetate and 136 mg of ammonium acetate as in Example 46, yielded 147 mg of 6-[(4-methylsuffonylphenyl)thio]-2,3-dihydro-2-(4-methoxyphenyl)5-methyl-3-oxo-4-pyridazinecarbonitrile, mp 187°–189° C.(EtOH).

$^1$H NMR(400 MHz, CDCl$_3$): 2.54 (s, 3H), 3.04(s, 3H), 3.80 (s, sH), 6.87 (d, J=9.2 Hz, 2H), 7.36 (d, J=8.8 Hz, 2H), 7.60 (d, J=8.8 Hz, 2H), 7.92 (d, J=8.8 Hz, 2H).

PBBI-NH$_3$/CI-MS Calculated for $C_{20}H_{17}N_3O_4S_2$ (427.5); Found 428 M(M+1), 430.

EXAMPLE 76

Preparation of 6-[(4-isopropylphenyl)thio]-2,3-dihydro-2-(4-methoxyphenyl)5-methyl-3 -oxo-4-pyridazinecarbonitrile The reaction of 221 mg of 1-[(isopropylphenyl)thio]-1-[4-methoxyphenyl)hydrazono]-2-propanone, 165 ul of ethylcyano acetate and 86 g of ammonium acetate as in Example 46, yielded 86 mg of 6-[(4-isopropylphenyl)thio]-2,3-dihydro-2-(4-methoxyphenyl)5-methyl-3-oxo-4-pyridazinecarbonitrile, mp 141°–144° C.(EtOH).

$^1$H NMR(400 MHz, CDCl$_3$) 1.24 (d, J=6.8 Hz, 6H), 2.53 (s, 3H), 2.91 (m, 1H), 3.77 (s, 3H), 6.78 (d, J=9.2 Hz), 2H), 7.23 (d, J=8.3 Hz, 2H), 7.34 (d, J=9.2 Hz, 2H), 7.39 (d, J=8.3 Hz, 2H).

PBBI-NH$_3$/CI-MS Calculated for $C_{22}H_{21}N_3O_2S$ (391.5); Found 3.92 (M+1)

EXAMPLE 77

Preparation of 6-[(4-phenylphenyl)thio]-2,3-dihydro-2-(4-methoxyphenyl)5-methyl-3 -oxo-4-pyridazinecarbonitrile The reaction of 280 mg (0.744 mmol) of 1-[(4-phenylphenyl)thio]-1 -[4-methoxyphenyl)hydrazono]-2-propanone, 190 ul of ethylcyano acetate and 63 mg of ammonium acetate as in Example 46, yielded 110 mg of 6-[(4-phenylphenyl)thio]-2,3-dihydro-2-(4-methoxyphenyl) 5-methyl-3-oxo-4-pyridazinecarbonitrile, mp 205°–207° C. (HOAc).

$^1$H NMR(400 MHz, CDCl$_3$): 2.56 (s, 3H), 3.76 (s, 3H), 6.80 (, J=8.8 Hz, 2H),7.36 (m, 1H) 7.37 (d, J=8.8 Hz, 2H), 7.45 (m, 2H), 7.5 1 (m, 6 H).

PBBI-NH$_3$/CI-MS Calculated for $C_{25}H_{19}N_3O_2S$ (425.5); Found 426 (M+1)

EXAMPLE 78

Preparation of 6-[(4-chlorophenyl)thio]-2,3-dihydro-2-(3-methoxyphenyl)5-methyl-3 -oxo-4-pyridazinecarbonitrile The reaction of 838 mg of 1-[(4-chlorophenyl)thio]-1-[3-methoxyphenyl)hydrazono]-2-propanone, 714 ul of ethylcyano acetate and 358 mg of ammonium acetate as in Example 46, yielded 560 mg of 6-[(4-chlorophenyl)thio]-2,3 -dihydro-2-(3-methoxyphenyl)5-methyl-3-oxo-4-pyridazinecarbonitrile, mp 148°–149° C. (EtOH).

$^1$H NMR(400 MHz, CDCl$_3$): 2.54 (s, 3H), 3.70 (s, 3H), 6.85 (m, 1H), 6.89 (t, J=2Hz, 1H), 7.06 (m, 1H), 7,23 (m, 1H), 7.36 (d, J=8.8 Hz, 2H), 7.43 (d, J=8.8 Hz, 2H).

PBB I-NH$_3$/CI-MS Calculated for $C_{19}H_{14}C_{12}N_3O_2S$ (383.8); Found 384 (M+1)

EXAMPLE 79

Preparation of 6-[(4-chlorophenyl)thio]-2,3-dihydro-2-(4-nitrophenyl) 5-methyl-3-oxo-4-pyridazinecarbonitrile The reaction of 1.13 g of 1-[(4-chlorophenyl)thio]-1-[4-notrophenyl)hydrazono]-2-propanone, 828 ul of ethylcyano acetate and 412 mg of ammonium acetate as in Example 46, yielded 310 mg of 6-[(3,4-dichlorophenyl)thio]-2,3-dihydro-2-(3-methoxyphenyl5-methyl-3-oxo-4-pyridazinecarbonitrile, mp 187°–189° C.(EtOH)

$^1$H NMR(400 MHz, CDCl$_3$): 2.59 (s, 3H), 7.44 (d, J=9 Hz, 2H), 7.64 (d, J=9 Hz, 2H), 7.63 (d, J=9.2 Hz,2H), 8.17 (d, J=9.2 Hz, 2H).

PBBI-NH$_3$/CI-MS Calculated for C$_{18}$H$_{11}$C$_1$N$_4$O$_3$S (398.8); Found 399 (M+1)

EXAMPLE 80

Preparation of 6-[(4-chlorophenyl)thio]-2,3-dihydro-22-(4-phenoxyphenyl)5-methyl-3-oxo-4-pyridazinecarbonitrile The reaction of 433 mg (1.08 mmol) of 1-[(4-chlorophenyl)thio]-1-[4-phenoxyoxyphenyl)hydrazono]-2-propanone, 275 ul of ethylcyano acetate and 137 mg of ammonium acetate as in Example 46, yielded 290 mg of 6-[(4-chlorophenyl)thio]-2,3-dihydro-2-(4-phenoxyphenyl) 5-methyl-3-oxo-4-pyridazinecarbonitrile, mp 163.5°–164.5° C.(EtOH)

$^1$H NMR(400 MHz, CDCl$_3$): 2.54 (s, 3H), 6.93 (d, J=9 Hz, 2H), 7.01 (dd J=8 Hz, 2 Hz, 2H), 7.13 (dt, J=8.4, 2 Hz, 1H), 7.37 (m, 8 H).

PBBI-NH$_3$/CI-MS Calculated for C$_{24}$H$_{16}$ClN$_3$O$_2$S (445.93); Found 446 (M+1)

EXAMPLE 81

Preparation of 6-[(4-chlorophenyl)thio]-2,3-dihydro-2-(4-methylsulfonylphenyl)5-methyl-3-oxo-4-pyridazinecarbonitrile The reaction of 375 mg (0.979 mmol) of 1-[(4-chlorophenyl)thio]-1-[4-methylsulfonylphenyl)hydrazono]-2-propanone, 250 ul of ethylcyano acetate and 124 mg of ammonium acetate as in Example 46 yielded 170 mg of 6-[(4-chlorophenyl)thio]-2,3-dihydro-2-(4-methylsulfonylphenyl)5-methyl-3-oxo-4-pyridazinecarbonitrile, mp 199°–201° C. (EtOH)

$^1$H NMR(400 MHz, CDCl$_3$): 2.55 (s, 3H), 3.03 (s, 3H), 7.40 (d, J =9 Hz, 2H), 7.48 (d, J=9 Hz, 2H), 7.64, (d, J=8.8 Hz, 2H), 7.90 (d, J =8.8 Hz, 2H).

PBBI-NH$_3$/CI-MS Calculated for C$_{19}$H$_{14}$C$_1$N$_3$O$_3$S$_2$ (431.9) Found 432 (M+1)

EXAMPLE 82

Preparation of 6-[(4-chlorophenyl)thio]-2,3-dihydro-2-(3, 4-methylenedioxyphenyl)5-methyl-3-oxo-4-pyridazinecarbonitrile The reaction of 100 mg of 1-[(4-chlorophenyl)thio]-1-[3, 4-methylenedioxyphenyl)hydrazono]-2-propanone, 80 ul of ethylcyano acetate and 38 mg of ammonium acetate as in Example 46 yielded 30 mg of 6-[(4-chlorophenyl)thio]-2,3-dihydro-2-(3, 4-methylenedioxyphenyl) 5-methyl-3-oxo-4-pyridazinecarbonitrile, mp 166°–168.5° C. (EtOH)

$^1$H NMR(400 MHz, CDCl$_3$): 2.52 (s, 3H), 5.98 (s, 2H), 7.23 ( d, J=9.0 H.z, 1H), 6.86(m, 2H), 7.36 (d, J=8.8 Ha:, 2H), 7.40 (d, J=8.8 Hz, 2H).

PBBI-NH$_3$/CI-MS Calculated for C$_{19}$H$_{13}$ClN$_3$O$_3$S (398.8) Found 399 (M+1)

EXAMPLE 83

Preparation of 6-[(4-chlomphenyl)thio]-2,3-dihydro-2-(4-methylthiophenyl)5-methyl-3-oxo-4-pyridazinecarbonitrile The reaction of 343 mg (1.08 mmol) of 1-[(4-chlorophenyl)thio]-1-[4-methylthiophenyl)hydrazono]-2-propanone, 274 ul of ethylcyano acetate and 134 mg of ammonium acetate as in Example 46 yielded 340 mg of 6-[(4-chlorophenyl)thio]-2,3-dihydro-2-(4-methylthiophenyl)5-methyl-3 -oxo-4-pyridazinecarbonitrile, mp 158°–160° C. (EtOH)

$^1$H NMR(400 MHz, CDCl$_3$): 2.46 (s, 3H), 2.54 (s, 3H), 7.17 (d, J=8.8 Hz, 2H), 7.32 (d, J=8.8 Hz, 2H), 7.37(d, J=8.8 Hz, 2H), 7.42 (d, J=8.8 Hz, 2H).

EXAMPLE 84

Preparation of 6-[(4-chlorophenyl)thio]-2,3-dihydro-2-(4-t-butoxyphenyl)5-methyl-3 -oxo-4-pyridazinecarbonitrile The reaction of of 1-[(4-chlorophenyl)thio]-1-[4-t-butoxy-phenyl)hydrazono]-2-propanone, ethylcyano acetate and ammonium acetate as in Example 46 yields 6-[(4-chlorophenyl)thio]-2,3-dihydro-2- (4-t-butoxyphenyl)5 -methyl-3 -oxo-4-pyridazinecarbonitrile.

EXAMPLE 85

Preparation of 1-chloro-1-[(4-methoxyphenyl) hydrazono]-2-propanone

A preferred method for the preparation of the titled compound is as follows:

A vigorously stirred suspension of 49.2g (0:339 mole) of 4-methoxy-aminobenzene in 400 ml of 5N hydrochloric acid was cooled to 0° C. and treated, dropwise, width 30.4 g (0,440 mol) of sodium nitrite dissolved in 100 ml of water. The temperature was maintained at 0°–5° C.+/–1° during the addition. After addition was complete, the reaction mixture was stirred at 0° C.+/–1° for an additional 30 min. The cold diazonium solution was poured slowly into a vigorously stirred solution of 54 g (0.401 mol) of 3-chloro-2,4-pentanedione dissolved in 280 ml of pyridine and 280 ml of water precoolcd to -8° C.+/–1°. The ice bath was removed and the resultant yellow suspension was stirred at 5° C.+/–1° for 30 minutes, diluted with 500 ml of water. The yellow solids were collected by filtration and washed with 300 ml water (4 times). The wet crude product was dissolved in 500 rnI of methylene chloride. The organic layer was dried over magnesium sulfate, filtered and evaporated in vacuo to yield 56.45 g of 1-chloro-1-[(4-methoxyphenyl)hydrazono]-2-propanone. The purity of the product was sufficient for further utilization. Further purification was accomplished by chromatography over silica gel and elution with elution with n-hexane:ethyl acetate (3:1) to yield 1-chloro-1 -[(4-methoxyphenyl)hydrazono]-2-propanone, mp 114°–116° C. (hexane).

$^1$H NMR(400MHz, CDCl$_3$): 2.53 (s,3H), 3.79 (s3H) 6.89 (d, J=9Hz, 2H), 7.24 (d, J=9Hz, 2H), 8.36 (broad s, 1H);

PBBI-NH$_3$/CI-MS Calculated for C$_{10}$H$_{11}$C$_1$N$_2$O$_2$(226.6); found: 227 (M+1), 123

EXAMPLE 86

T Cell Proliferation Assay

Spleens form C$_{57}$B 1/6 mice were taken under sterile conditions and gently dissociated in ice-cold RPMI 1640 culture medium (GIBC, Grand Island, N.Y.)supplemented with 10% heat inactivated fetal calf serum (GIBO). Cells were pelleted by centrifugation at 1500 rpm for 8 minutes. Contaminating red cells were removed by treating the pellet with ammonium chloride lysing buffer (GIBO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were pipaxed by packing approximately 4 gms of washed and dried nylon wool into 20 ml plastic syringes. The columns were sterilized by autoclaving at 25° F. for 30 minutes. Nylon columns were wetted with warm (37° C.) culture medium and rinsed with the same medium. Washed spleen cells resuspended in warm medium were slowly applied to the nylon wool. The colms were then incubated in an upright position at 37° C. for 1 hour. Non-adherent T lymphocytes were eluted from columns with warm culture medium and the cell suspensions were spun as described above. Purified T lymphocytes were resuspended at $2.5\times10^5$ cells/ml in complete culture medium composed of RPMI 1640 medium with 10% heat-inactivated fetal calf serum, 100 mM glutamine, 1 mM sodium pyruvate, $2\times10^5$-M 2-mercaptoethanol and 50 ug/ml gentamycin. Ionomycin was added at 250 ng/ml and PMA at 10 ng/ml. The cell suspension was immediately distributed into 96 well flat-bottom microculture plates (Costar) at 200 ul/well. The various dilutions of test compound were then added in triplicate wells at 20 ul/well. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 uCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scinfillation counting methods (Betacounter). Mean counts per minute of replicate wells were calculated and the results were expressed as concentration of compound required to inhibit tritiated thymidine uptake of T cells by 50%. While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

EXAMPLE 87

T Cell IL-2 Assay

Peripheral blood mononuclear cells from healthy donors were separated by density centrifugation with ficoll-hypaque (LSM, Organon Teknika, Durham, N.C.), followed by rosetting with neuraminidase treated SRBC. After another centrifugation with ISM, the SRBC of the rosetted T cells were then lysed with ammonium chloride lysing buffer (GIBCO). Such purified T cells were resuspended at $3\times10^6$/ml in RPMI 1640 culture medium (GIBCO, Grand Island, N.Y.) supplemented with 10% fetal calf serum (HyClone Laboratories, Logan, Utah), 100 mM glutamine, 1 mM sodium pyruvate, 0.1 mM non-essential amino acids, and 1% perm-strep (GIBCO). The cell suspension was immediately distributed into 96 well round-bottom microculture plates (Costar) at 200 ul/well. The various dilutions of test compound were then added in triplicate wells at 25 ul/well, incubated for 15 min at 37° C. Ionomycin (125 ng/ml), anti-CD28 (100 ng/ml) and PMA (1 or 5 ng/ml, with ionomycin or anti-CD28, respectively) were added to the appropriate wells. The culture plates were then incubated at 37° C. in a humidified atmosphere of 5% $CO_2$-95% air for 24 hours. The supernatants were removed, and assayed for IL-2 with an IL-2 ELISA Kit (Collaborative Biomedical Products, Bedford. Mass.). Mean OD and units of IL-2 of the replicate wells were calculated and the results were expressed as concentration of compound required to inhibit IL-2 production of T cells by 50%.

What is claimed is:

1. A compound of formula I

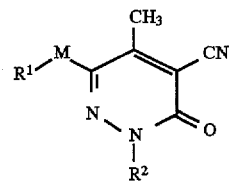

or a pharmaceutically acceptable salt, hydrate or crystal form thereof, wherein:

M is $S(O)_p$, p is 0, 1 or 2, $R^1$ and $R^2$ are selected from:
  (a) aryl;
  (b) substituted aryl in which as many as three substituents, X, Y, and Z, may be present;

X, Y and Z independently are selected from:
  (a) hydrogen, except that when $R^1$ is 4-chlorophenyl, then $R^2$ can not be phenyl,
  (b) $C_{1-10}$ alkyl, unsubstituted or substituted with a substituent selected from the group consisting of:
    (i) aryl,
    (ii) $C_{1-6}$ alkoxy,
    (iii) —$NO_2$
    (iv) —$NR^3R^4$,
    (v) —$CO_2H$,
    (vi) —OH, and
    (vii) oxo;
    except that when $R^2$ is 2-methyl-phenyl—, 3-methyl-phenyl, or 4-methyl-phenyl, then $R^1$ can not be 4-chloro-phenyl-;
  (c) $C_{1-10}$ alkoxy, unsubstituted or substituted with a substituent selected from the group consisting of:
    (i) aryl,
    (ii) $C_{1-6}$ alkoxy,
    (iii) —$NO_2$
    (iV) —$NR^3R^4$,
    (v) —$CO_2H$,
    (vi) —OH, and
    (vii) oxo;
    except that when $R^2$ is 4-methoxyphenyl, then $R^1$ is not 4-chlorophenyl, phenyl or —$SO_2$-phenyl;
  (d) aryl,
  (e) aryloxy,
  (f) halogen, except that when $R^2$ is 2-chlorophenyl, 3-chlorophenyl, 4-chlorophenyl or 4-bromophenyl, then $R^1$ is not 4-chlorophenyl,
  (g) —$NO_2$, except that when $R^2$ is 3-nitrophenyl, then $R^1$ is not 4-chlorophenyl,
  (h) —$NR^3R^4$,
  (i) —CN,
  (k) —$CF_3$,
  (l) —$S(O)_pR^7$, wherein $R^7$ is hydrogen, $C_{1-6}$ alkyl, trifluoromethyl, or phenyl, except that when X, Y or Z is $S(O)_pR^7$, then M cannot be SO or $SO_2$,
  (m) —$CH(OR^8)(OR^9)$,
  (n) OH, and
  (o) $OCF_3$, provided that p is 0, $R^1$ is phenyl, and $R^2$ is phenyl substituted with methoxy;

$R^3$ and $R^4$ are independently selected from:
(a) hydrogen,
(b) $C_{1-6}$ alkyl unsubstituted or substituted, wherein the substituted group is selected from:
  (i) —OH,
  (ii) —$C_{1-6}$ alkoxy,
  (iii) —$CO_2H$,
  (iv) oxo,
  (v) —$C_{3-7}$ cycloalkyl, and
  (vi) —$C_{1-6}$ alkyl—OH;

$R^8$ and $R^9$ are $C_{1-3}$ alkyl or taken together form an ethyl or propyl bridge; $M^+$ is a positively charged inorganic or organic counterion, n is 1 or 2;

q is 1, 2 or 3;

aryl is defined in all instances above as phenyl or naphthyl; and aryloxy is defined in all instances above as phenoxy or naphthyloxy;

provided that when M represents S and more than one of X, Y or Z represents $S(O)_pR^7$, then p represents the same number of oxygen atoms on $S(O)_pR^7$; and when M is SO or $SO_2$, then X, Y or Z cannot represent $S(O)_pR^7$.

2. The compound of claim 1 wherein:

M is $S(O)_p$;

p is 0, 1 or 2;

$R^1$ and $R^2$ are selected from: substituted aryl in which as many as three substituents, X, Y, and Z, may be present;

X, Y and Z independently are selected from:
(a) hydrogen, except that when $R^1$ is 4-chlorophenyl, then $R^2$ can not be phenyl,
(b) $C_{1-10}$ alkyl, unsubstituted or substituted with a substituent selected from the group consisting of:
  (i) aryl,
  (ii) $C_{1-6}$ alkoxy,
  (iii) —$NO_2$,
  (iv) —$NR^3R^4$,
  (v) —$CO_2H$,
  (vi) —OH, and
  (vii) oxo;
  except that when $R^2$ is 2-methylphenyl—, 3-methylphenyl, or 4-methyl-phenyl, then $R^1$ can not be 4-chloro-phenyl-;
(c) $C_{1-10}$ alkoxy, unsubstituted or substituted with a substituent selected from the group consisting of:
  (i) aryl,
  (ii) $C_{1-6}$ alkoxy,
  (iii) —$NO_2$,
  (iv) —$NR^3R^4$,
  (v) —$CO_2H$,
  (vi) —OH, and
  (vii) oxo;
  except that when $R^2$ is 4-methoxyphenyl, then $R^1$ is not 4-chloro-phenyl, phenyl or —$SO_2$-phenyl;
(d) aryl,
(e) aryloxy,
(f) halogen, except that when $R^2$ is 2-chlorophenyl, 3-chlorophenyl, 4-chlorophenyl or 4-bromophenyl, then $R^1$ is not 4-chloro-phenyl;
(g) —$NO_2$, except that when $R^2$ is 3-nitrophenyl, then $R^1$ is not 4-chlorophenyl,
(h) —$NR^3R^4$,
(i) —CN,
(k) —$CF_3$,
(l) —$S(O)_pR^7$, wherein $R^7$ is hydrogen, $C_{1-6}$ alkyl, trifluoromethyl, or phenyl, except that when X, Y or Z is $S(O)_pR^7$, then M cannot be SO or $SO_2$,
(m) —$CH(OR^8)(OR^9)$,
(n) OH, and
(o) $OCF_3$, provided that p is 0, $R^1$ is phenyl, and $R^2$ is phenyl substituted with methoxy;

$R^3$ and R4 are independently selected from:
(a) hydrogen,
(b) $C_{1-6}$ alkyl unsubstituted or substituted, wherein the substituted group is selected from:
  (i) —OH,
  (ii) —$C_{1-6}$ alkoxy,
  (iii) —$CO_2H$,
  (iv) oxo,
  (v) —$C_{3-7}$ cycloalkyl, and
  (vi) —$C_{1-6}$ alkyl—OH;

$R^8$ and $R^9$ are $C_{1-3}$ alkyl or taken together form an ethyl or propyl bridge; $M^+$ is a positively charged inorganic or organic counterion, n is 1 or 2;

q is 1, 2 or 3;

aryl is defined in all instances above as phenyl or naphthyl; and aryloxy is defined in all instances above as phenoxy or naphthyloxy;

provided that when M represents S and more than one of X, Y or Z represents $S(O)_pR^7$, then p represents the same number of oxygen atoms on $S(O)_pR^7$; and when M is SO or $SO_2$, then X, Y or Z cannot represent $S(O)_pR^7$.

3. A compound of formula or a pharmaceutically accceptable salt, hydrate or crystal form thereof, where M is S, SO or $SO_2$ and $R^1$ and $R^2$ are selected from Table 1:

TABLE 1

| $R^1$ | $R^2$ |
|---|---|
| phenyl | phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-$CH_3$Ophenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-$NO_2$phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-$CH_3$Sphenyl |
| 2-methylphenyl | " |
| 3-methylphenyl | " |

TABLE 1-continued

| R¹ | R² |
|---|---|
| 4-methylphenyl | " |
| 3,4-dimethylphenyl | " |
| 3,5-dimethylphenyl | " |
| phenyl | 3-CH₃SOphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3-CH₃SO₂phenyl |
| 2-methylphenyl | " |
| 3-methylphenyl | " |
| 4-methylphenyl | " |
| 3,4-dimethylphenyl | " |
| 3,5-dimethylphenyl | " |
| 2-methylphenyl | 4-CH₃Ophenyl |
| 3-methylphenyl | " |
| 4-methylphenyl | " |
| 3,4-dimethylphenyl | " |
| 3,5-dimethylphenyl | " |
| phenyl | 4-NO₂phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 4-CH₃Sphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 4-CH₃SOphenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 4-CH₃SO₂phenyl |
| 2-methylphenyl | " |
| 3-methylphenyl | " |
| 4-methylphenyl | " |
| 3,4-dimethylphenyl | " |
| 3,5-dimethylphenyl | " |
| phenyl | 3,4-OCH₂Ophenyl |
| 2-methylphenyl | " |
| 3-methylphenyl | " |
| 4-methylphenyl | " |
| 3,4-dimethylphenyl | " |
| 3,5-dimethylphenyl | " |
| 2-CH₃Ophenyl | Phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-CH₃Ophenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-NO₂phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-CH₃Sphenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-CH₃SOphenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3-CH₃SO₂phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 4-CH₃Ophenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃OPhenyl | 4-NO₂phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 4-CH₃Sphenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 4-CH₃SOphenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 4-CH₃SO₂Phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Ophenyl | 3,4-CH₂OCH₂phenyl |
| 3-CH₃Ophenyl | " |
| 4-CH₃Ophenyl | " |
| 3,4-bis-CH₃Ophenyl | " |
| 3,5-bis-CH₃Ophenyl | " |
| 2-CH₃Sphenyl | Phenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 3-CH₃Ophenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 3-NO₂phenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 3-CH₃Sphenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 4-CH₃Ophenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 4-NO₂phenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 4-CH₃Sphenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃Sphenyl | 3,4-CH₂OCH₂Phenyl |
| 3-CH₃Sphenyl | " |
| 4-CH₃Sphenyl | " |
| 3,4-bis-CH₃Sphenyl | " |
| 3,5-bis-CH₃Sphenyl | " |
| 2-CH₃SOphenyl | Phenyl |
| 3-CH₃SOphenyl | " |
| 4-CH₃SOphenyl | " |
| 3,4-bis-CH₃SOphenyl | " |

TABLE 1-continued

| R¹ | R² |
|---|---|
| 2-CH₃SOphenyl | 3-CH₃Ophenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 3-NO₂phenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 3-CH₃Sphenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 4-CH₃Ophenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 4-NO₂phenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 4-CH₃SOphenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SOphenyl | 3,4-CH₂OCH₂phenyl |
| 3-CH₃SOphenyl | " |
| 4-CH₃SOphenyl | " |
| 3,4-bis-CH₃SOphenyl | " |
| 3,5-bis-CH₃SOphenyl | " |
| 2-CH₃SO₂phenyl | Phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 3-CH₃Ophenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 3-NO₂phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 3-CH₃SO₂phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 4-CH₃Ophenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 4-NO₂phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 4-CH₃SO₂phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-CH₃SO₂phenyl | 3,4-CH₂OCH₂phenyl |
| 3-CH₃SO₂phenyl | " |
| 4-CH₃SO₂phenyl | " |
| 3,4-bis-CH₃SO₂phenyl | " |
| 3,5-bis-CH₃SO₂phenyl | " |
| 2-Clphenyl | phenyl |
| 3-Clphenyl | " |
| 3,4-di-Clphenyl | " |
| 3,5-di-Clphenyl | " |
| 2-Clphenyl | 3-CH₃Ophenyl |
| 3-Clphenyl | " |
| 4-Clphenyl | " |
| 3,4-di-Clphenyl | " |
| 3,5-Clphenyl | " |
| 2-Clphenyl | 3-NO₂phenyl |
| 3-Clphenyl | " |
| 3,4-di-Clphenyl | " |
| 3,5-Clphenyl | " |
| 2-Clphenyl | 3-CH₃Sphenyl |
| 3-Clphenyl | " |
| 4-Clphenyl | " |
| 3,4-di-Clphenyl | " |
| 3,5-Clphenyl | " |
| 2-Clphenyl | 3-CH₃SOphenyl |
| 3-Clphenyl | " |
| 4-Clphenyl | " |
| 3,4-di-Clphenyl | " |
| 3,5-Clphenyl | " |
| 2-Clphenyl | 3-CH₃SO₂phenyl |
| 3-Clphenyl | " |
| 4-Clphenyl | " |
| 3,4-di-Clphenyl | " |
| 3,5-Clphenyl | " |
| 2-Clphenyl | 4-CH₃Ophenyl |
| 3-Clphenyl | " |
| 3,4-Clphenyl | " |
| 3,5-Clphenyl | " |
| 2-Clphenyl | 4-NO₂phenyl |
| 3-Clphenyl | " |
| 4-Clphenyl | " |
| 3,4-Clphenyl | " |
| 3,5-Clphenyl | " |
| 2-Clphenyl | 4-CH₃Sphenyl |
| 3-Clphenyl | " |
| 4-Clphenyl | " |
| 3,4-Clphenyl | " |
| 3,5-Clphenyl | " |
| 2-Clphenyl | 4-CH₃SOphenyl |
| 3-Clphenyl | " |
| 4-Clphenyl | " |
| 3,4-Clphenyl | " |
| 3,5-Clphenyl | " |
| 2-Clphenyl | 4-CH₃SO₂phenyl |
| 3-Clphenyl | " |
| 4-Clphenyl | " |
| 3,4-Clphenyl | " |
| 3,5-Clphenyl | " |
| 2-Clphenyl | 3,4-CH₂OCH₂phenyl |
| 3-Clphenyl | " |
| 4-Clphenyl | " |
| 2-CF₃phenyl | phenyl |
| 3-CF₃phenyl | " |
| 4-CF₃phenyl | " |
| 3,4-di-CF₃phenyl | " |
| 3,5-diCF₃phenyl | " |
| 2-CF₃phenyl | 3-CH₃Ophenyl |
| 3-CF₃phenyl | " |
| 4-CF₃phenyl | " |
| 3,4-di-CF₃phenyl | " |
| 3,5-CF₃phenyl | " |
| 2-CF₃phenyl | 3-NO₂phenyl |
| 3-CF₃phenyl | " |
| 4-CF₃phenyl | " |
| 3,4-di-CF₃phenyl | " |
| 3,5-CF₃phenyl | " |
| 2-CF₃phenyl | 3-CH₃Sphenyl |
| 3-CF₃phenyl | " |
| 4-CF₃phenyl | " |
| 3,4-di-CF₃phenyl | " |
| 3,5-CF₃phenyl | " |
| 2-CF₃phenyl | 3-CH₃SOphenyl |
| 3-CF₃phenyl | " |
| 4-CF₃phenyl | " |
| 3,4-di-CF₃phenyl | " |

TABLE 1-continued

| R¹ | R² |
|---|---|
| 3,5-CF₃phenyl | " |
| 2-CF₃phenyl | 3-CH₃SO₂phenyl |
| 3-CF₃phenyl | " |
| 4-CF₃phenyl | " |
| 3,4-di-CF₃phenyl | " |
| 3,5-CF₃phenyl | " |
| 2-CF₃phenyl | 4-CH₃Ophenyl |
| 3-CF₃phenyl | " |
| 4-CF₃phenyl | " |
| 3,4-CF₃phenyl | " |
| 3,5-CF₃phenyl | " |
| 2-CF₃phenyl | 4-NO₂phenyl |
| 3-CF₃phenyl | " |
| 4-CF₃phenyl | " |
| 3,4-CF₃phenyl | " |
| 3,5-CF₃phenyl | " |
| 2-CF₃phenyl | 4-CH₃Sphenyl |
| 3-CF₃phenyl | " |
| 4-CF₃phenyl | " |
| 3,4-CF₃phenyl | " |
| 3,5-CF₃phenyl | " |
| 2-CF₃phenyl | 4-CH₃SOphenyl |
| 3-CF₃phenyl | " |
| 4-CF₃phenyl | " |
| 3,4-CF₃phenyl | " |
| 3,5-CF₃phenyl | " |
| 2-CF₃phenyl | 4-CH₃SO₂phenyl |
| 3-CF₃phenyl | " |
| 4-CF₃phenyl | " |
| 3,4-CF₃phenyl | " |
| 3,5-CF₃phenyl | " |
| 2-CF₃phenyl | 3,4-CH₂OCH₂phenyl |
| 3-CF₃phenyl | " |
| 4-CF₃phenyl | " |
| 3,4-CF₃phenyl | " |
| 3,5-CF₃phenyl | " |
| 2-Fphenyl | phenyl |
| 3-Fphenyl | " |
| 4-Fphenyl | " |
| 3,4-di-Fphenyl | " |
| 3,5-diFphenyl | " |
| 2-Fphenyl | 3-CH₃Ophenyl |
| 3-Fphenyl | " |
| 4-Fphenyl | " |
| 3,4-di-Fphenyl | " |
| 3,5-Fphenyl | " |
| 2-Fphenyl | 3-NO₂phenyl |
| 3-Fphenyl | " |
| 4-Fphenyl | " |
| 3,4-di-Fphenyl | " |
| 3,5-Fphenyl | " |
| 2-Fphenyl | 3-CH₃Sphenyl |
| 3-Fphenyl | " |
| 4-Fphenyl | " |
| 3,4-di-Fphenyl | " |
| 3,5-Fphenyl | " |
| 2-Fphenyl | 3-CH₃SOphenyl |
| 3-Fphenyl | " |
| 4-Fphenyl | " |
| 3,4-di-Fphenyl | " |
| 3,5-Fphenyl | " |
| 2-Fphenyl | 3-CH₃SO₂phenyl |
| 3-Fphenyl | " |
| 4-Fphenyl | " |
| 3,4-di-Fphenyl | " |
| 3,5-Fphenyl | " |
| 2-Fphenyl | 4-CH₃OPhenyl |
| 3-Fphenyl | " |
| 4-Fphenyl | " |
| 3,4-Fphenyl | " |
| 3,5-Fphenyl | " |
| 2-Fphenyl | 4-NO₂phenyl |
| 3-Fphenyl | " |
| 4-Fphenyl | " |
| 3,4-Fphenyl | " |
| 3,5-Fphenyl | " |
| 2-Fphenyl | 4-CH₃SOphenyl |
| 3-Fphenyl | " |
| 4-Fphenyl | " |
| 3,4-Fphenyl | " |
| 3,5-Fphenyl | " |
| 2-Fphenyl | 4-CH₃SO₂phenyl |
| 3-Fphenyl | " |
| 4-Fphenyl | " |
| 3,4-Fphenyl | " |
| 3,5-Fphenyl | " |
| 2-Fphenyl | 3,4-CH₂OCH₂phenyl |
| 3-Fphenyl | " |
| 4-Fphenyl | " |
| 3,4-Fphenyl | " |
| 3,5-Fphenyl | " |
| 2-ethylphenyl | phenyl |
| 3-ethylphenyl | " |
| 4-ethylphenyl | " |
| 3,4-diethylphenyl | " |
| 3,5-diethylphenyl | " |
| 2-ethylphenyl | 3-CH₃Ophenyl |
| 3-ethylphenyl | " |
| 4-ethylphenyl | " |
| 3,4-diethylphenyl | " |
| 3,5-diethylphenyl | " |
| 2-ethylphenyl | 3-NO₂phenyl |
| 3-ethylphenyl | " |
| 4-ethylphenyl | " |
| 3,4-diethylphenyl | " |
| 3,5-diethylphenyl | " |
| 2-ethylphenyl | 3-CH₃Sphenyl |
| 3-ethylphenyl | " |
| 4-ethylphenyl | " |
| 3,4-diethylphenyl | " |
| 3,5-diethylphenyl | " |
| 2-ethylphenyl | 3-CH₃SOphenyl |
| 3-ethylphenyl | " |
| 4-ethylphenyl | " |
| 3,4-diethylphenyl | " |
| 3,5-diethylphenyl | " |
| 2-ethylphenyl | 3-CH₃SO₂phenyl |
| 3-ethylphenyl | " |
| 4-ethylphenyl | " |
| 3,4-diethylphenyl | " |
| 3,5-diethylphenyl | " |
| 2-ethylphenyl | 4-CH₃Ophenyl |
| 3-ethylphenyl | " |
| 4-ethylphenyl | " |
| 3,4-diethylphenyl | " |
| 3,5-diethylphenyl | " |
| 2-ethylphenyl | 4-NO₂phenyl |
| 3-ethylphenyl | " |
| 4-ethylphenyl | " |
| 3,4-diethylphenyl | " |
| 3,5-diethylphenyl | " |
| 2-ethylphenyl | 4-CH₃Sphenyl |
| 3-ethylphenyl | " |
| 4-ethylphenyl | " |
| 3,4-diethylphenyl | " |
| 3,5-diethylphenyl | " |
| 2-ethylphenyl | 4-CH₃SOphenyl |
| 3-ethylphenyl | " |
| 4-ethylphenyl | " |
| 3,4-diethylphenyl | " |
| 3,5-diethylphenyl | " |
| 2-ethylphenyl | 4-CH₃SO₂phenyl |
| 3-ethylphenyl | " |
| 4-ethylphenyl | " |
| 3,4-diethylphenyl | " |
| 3,5-diethylphenyl | " |
| 2-ethylphenyl | 3,4-CHOCH₂phenyl |
| 3-ethylphenyl | " |
| 4-ethylphenyl | " |
| 3,4-diethylphenyl | " |
| 3,5-diethylphenyl | " |
| 2-phenylphenyl | phenyl |
| 3-phenylphenyl | " |
| 4-phenylphenyl | " |

TABLE 1-continued

| R¹ | R² |
|---|---|
| 2-phenylphenyl | 3-CH₃Ophenyl |
| 3-phenylphenyl | " |
| 4-phenylphenyl | " |
| 2-phenylphenyl | 3-NO₂phenyl |
| 3-phenylphenyl | " |
| 4-phenylphenyl | " |
| 2-phenylphenyl | 3-CH₃Sphenyl |
| 3-phenylphenyl | " |
| 4-phenylphenyl | " |
| 2-phenylphenyl | 3-CH₃SOphenyl |
| 3-phenylphenyl | " |
| 4-phenylphenyl | " |
| 2-phenylphenyl | 3-CH₃SO₂phenyl |
| 3-phenylphenyl | " |
| 4-phenylphenyl | " |
| 2-phenylphenyl | 4-CH₃Ophenyl |
| 3-phenylphenyl | " |
| 4-phenylphenyl | " |
| 2-phenylphenyl | 4-NO₂phenyl |
| 3-phenylphenyl | " |
| 4-phenylphenyl | " |
| 2-phenylphenyl | 4-CH₃Sphenyl |
| 3-phenylphenyl | " |
| 4-phenylphenyl | " |
| 2-phenylphenyl | 4-CH₃SOphenyl |
| 3-phenylphenyl | " |
| 4-phenylphenyl | " |
| 2-phenylphenyl | 4-CH₃SO₂phenyl |
| 3-phenylphenyl | " |
| 4-phenylphenyl | " |
| 2-phenylphenyl | 3,4-CH₂OCH₂phenyl |
| 3-phenylphenyl | " |
| 4-phenylphenyl | " |
| 2-phenoxyphenyl | phenyl |
| 3-phenoxyphenyl | " |
| 4-phenoxyphenyl | " |
| 2-phenoxyphenyl | 3-CH₃Ophenyl |
| 3-phenoxyphenyl | " |
| 4-phenoxyphenyl | " |
| 2-phenoxyphenyl | 3-NO₂phenyl |
| 3-phenoxyphenyl | " |
| 4-phenoxyphenyl | " |
| 2-phenoxyphenyl | 3-CH₃Sphenyl |
| 3-phenoxyphenyl | " |
| 4-phenoxyphenyl | " |
| 2-phenoxyphenyl | 3-CH₃SOphenyl |
| 3-phenoxyphenyl | " |
| 4-phenoxyphenyl | " |
| 2-phenoxyphenyl | 3-CH₃SO₂phenyl |
| 3-phenoxyphenyl | " |
| 4-phenoxyphenyl | " |
| 2-phenoxyphenyl | 4-CH₃Ophenyl |
| 3-phenoxyphenyl | " |
| 4-phenoxyphenyl | " |
| 2-phenoxyphenyl | 4-NO₂phenyl |
| 3-phenoxyphenyl | " |
| 4-phenoxyphenyl | " |
| 2-phenoxyphenyl | 4-CH₃Sphenyl |
| 3-phenoxyphenyl | " |
| 4-phenoxyphenyl | " |
| 2-phenoxyphenyl | 4-CH₃SOphenyl |
| 3-phenoxyphenyl | " |
| 4-phenoxyphenyl | " |
| 2-phenoxyphenyl | 4-CH₃SO₂phenyl |
| 3-phenoxyphenyl | " |
| 4-phenoxyphenyl | " |
| 2-phenoxyphenyl | 3,4-CH₂OCH₂phenyl |
| 3-phenoxyphenyl | " |
| 4-phenoxyphenyl | " |
| naphth-1-yl | phenyl |
| " | 3-CH₃Ophenyl |
| " | 3-NO₂phenyl |
| " | 3-CH₃Sphenyl |
| " | 3-CH₃SO₂phenyl |
| " | 4-CH₃Ophenyl |
| " | 4-NO₂phenyl |
| " | 4-CH₃Sphenyl |
| " | 4-CH₃SO₂phenyl |
| " | 3,4-CH₂OCH₂phenyl |
| naphth-2-yl | phenyl |
| " | 3-CH₃Ophenyl |
| " | 3-NO₂phenyl |
| " | 3-CH₃Sphenyl |
| " | 3-CH₃SO₂phenyl |
| " | 4-CH₃Ophenyl |
| " | 4-NO₂Phenyl |
| " | 4-CH₃Sphenyl |
| " | 4-CH₃SO₂phenyl |
| " | 3,4-CH₂OCH₂phenyl |
| 5-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-methylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-chloronaphth-1-yl | phenyl |
| " | 3-CH₃Ophenyl |
| " | 3-NO₂phenyl |
| " | 3-CH₃Sphenyl |
| " | 3-CH₃SOphenyl |

TABLE 1-continued

| R¹ | R² |
|---|---|
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-chloronaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-phenylnaphth-1-yl | phenyl |
| " | 3-CH₃Ophenyl |
| " | 3-NO₂phenyl |
| " | 3-OH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-phenylnaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-CH₃Onaphth-1-yl | phenyl |
| " | 3-CH₃OPhenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-CH₃Onaphth-1-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-methylnaphth-2-yl | phenyl |
| " | 3-CH₃Ophenyl |
| " | 3-NO₂phenyl |

TABLE 1-continued

| R¹ | R² |
|---|---|
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-methylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-chloronaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-phenylnaphth-2-yl | Phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 7-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-phenylnaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 5-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 6-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂pheny |
| " | 4-CH₃Sphenyl |
| " | 4-CH₃SOphenyl |
| " | 4-CH₃SO₂phenyl |
| " | 3,4-OCH₂Ophenyl |
| 7-CH₃Onaphth-2-yl | phenyl |
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |
| 8-CH₃Onaphth-2-yl | phenyl |

TABLE 1-continued

| R¹ | R² |
|---|---|
| " | 3-CH₃Ophenyl |
| " | 3-NO₂phenyl |
| " | 3-CH₃Sphenyl |
| " | 3-CH₃SOphenyl |
| " | 3-CH₃SO₂phenyl |
| " | 4-CH₃Ophenyl |
| " | 4-NO₂phenyl |
| " | 4-CH₃Sphenyl |
| " | 4-CH₃SOphenyl |
| " | 4-CH₃SO₂phenyl |
| " | 3,4-OCH₂Ophenyl |

4. A compound of formula I, selected from the group consisting of:

- 6-[(4-chlorophenyl)sulfinyl]-2,3-dihydro-2-(4-methoxyphenyl)-5-methyl-3-oxo-pyridazinecarbonitrile;
- 6-[(4-chlorophenyl)sulfonyl]-2,3-dihydro-2-(4-methoxyphenyl)-5-methyl-3-oxo-pyridazinecarbonitrile;
- 6-[(4-chlorophenyl)thio]-2,3-dihydro-2-(4-hydroxyphenyl)-5-methyl-oxo-4-pyridazinecarbonitrile;
- 6-[(4-chlorophenyl)thio]-2,3-dihydro-2-(4-ethoxyphenyl)-5-methyl-oxo-4-pyridazinecarbonitrile;
- 6-[(3-chlorophenyl)thio]-2,3-dihydro-2-(4-methoxyphenyl)-5-methyl-oxo-4-pyridazinecarbonitrile;
- 6-[(3,4-dichlorophenyl)thio]-2,3-dihydro-2-(4-methoxyphenyl)-5-methyl-3-oxo-pyridazinecarbonitrile;
- 6-[(4-methoxyphenyl)thio]-2,3-dihydro-2-(4-methoxyphenyl)-5-methyl-3-pyridazinecarbonitrile;
- 6-[(4-nitrophenyl)thio]2,3-dihydro-2-(4-methoxyphenyl)-5-methyl-3-oxo-4-pyridazinecarbonitrile;
- 6-[(4-fluorophenyl)thio]-2,3-dihydro-2-(4-methoxyphenyl)-5-methyl-3-oxo-4-pyridazinecarbonitrile;
- 6-[(4-trifluorophenyl)thio]-2,3-dihydro-2-(4-methoxyphenyl)-5-methyl-3-oxo-4-pyridazinecarbonitrile;
- 6-[(3,5-dicloro-phenyl)thio]-2,3-dihydro-2-(4-methoxyphenyl)-5-methyl-3-oxo-4-pyridazinecarbonitrile;
- 6-[(3-methoxyphenyl)thio]-2,3-dihydro-2-(4-methoxyphenyl)-5-methyl-3-oxo-4-pyridazinecarbonitrile;
- 6-[(3,4-dimethoxyphenyl)thio]-2,3-dihydro-2-(4-methoxyphenyl)-5-methyl-3-oxo-4-pyridazinecarbonitrile;
- 6-[(4-trifluoromethoxyphenyl)thio]-2,3-dihydro-2-(4-methoxyphenyl)-5-methyl-3-oxo-4-pyridazinecarbonitrile;
- 6-[(4-cyanophenyl)thio]-2,3-dihydro-2-(4-methoxyphenyl)-5-methyl-3-oxo-4-pyridazinecarbonitrile;
- 6-[(4-methylthiophenyl)thio]-2,3-dihydro-2-(4-methoxyphenyl)-5-methyl-3-oxo-4-pyridazinecarbonitrile;
- 6-[(4-methylsulfinylphenyl)thio]-2,3-dihydro-2-(4-methoxyphenyl)-5-methyl-3-oxo-4-pyridazinecarbonitrile;
- 6-[(4-phenylphenyl)thio]-2,3-dihydro-2-(3-methoxyphenyl)-5-methyl-3-oxo-4-pyridazinecarbonitrile;
- 6-[(4-chlorophenyl)thio]-2,3-dihydro-2-(4-methoxyphenyl)-5-methyl-3-oxo-4-pyridazinecarbonitrile;
- 6-[(4-chlorophenyl)thio]-2,3-dihydro-2-(4-phenoxyphenyl)-5-methyl-3-oxo-4-pyridazinecarbonitrile;
- 6-[(4-chlorophenyl)thio]-2,3-dihydro-2-(4-methylsulfonylphenyl)-5-methyl-3-oxo-4-pyridazinecarbonitrile;
- 6-[(4-chlorophenyl)thio]-2,3-dihydro-2-(4-methylenedioxyphenyl)-5-methyl-3-oxo-4-pyridazinecarbonitrile;
- 6-[(4-chlorophenyl)thio]-2,3-dihydro-2-(4-methylthiophenyl)-5-methyl-3-oxo-4-pyridazinecarbonitrile;
- 6-[(4-chlorophenyl)thio]-2,3-dihydro-2-(4-butoxyphenyl)-5-methyl-3-oxo-4-pyridazinecarbonitrile;

5. A pharmaceutical formulation comprising a pharmaceutically acceptable carier and a therapeutically effective amount of the compound of claim 1 or a pharmaceutically acceptable salt, crystal form or hydrate thereof.

6. The pharmaceutical formulation of claim 5, comprising in addition, an antiproliferative agent selected from the group consisting of: azathioprine, brequinar sodium, deoxyspergualin, mizaribine, mycophenolic acid morpholino ester, cyclosporin, FK-506 and rapamycin.

* * * * *